United States Patent [19]
Zolg

[11] Patent Number: 5,525,463
[45] Date of Patent: Jun. 11, 1996

[54] METHOD AND REAGENTS FOR DETECTION OF MYCOBACTERIA USING SUPEROXIDE DISMUTASE GENE TARGETING

[75] Inventor: Werner Zolg, Rheinfelden, Germany

[73] Assignee: Hoffmann-La Roche Inc., Nutley, N.J.

[21] Appl. No.: 133,711

[22] Filed: Oct. 7, 1993

[30] Foreign Application Priority Data

Oct. 13, 1992 [EP] European Pat. Off. .............. 92810780

[51] Int. Cl.$^6$ .............................. C12Q 1/68; C12P 19/34; C07H 21/04
[52] U.S. Cl. ........................ 435/6; 435/91.2; 536/24.33; 536/24.32
[58] Field of Search ................. 435/6, 91.2; 536/24.33, 536/24.32

[56] References Cited

FOREIGN PATENT DOCUMENTS

| 479117 | 9/1991 | European Pat. Off. . |
|---|---|---|
| WO91/03558 | 9/1990 | WIPO . |
| WO92/05280 | 9/1991 | WIPO . |

OTHER PUBLICATIONS

Zhang et al. (1992) Infection & Immunity 60(6):2160–2165.
Thangaraj et al. (1990) Infect. Immun. 58(6): 1937–1942.
Colston (1990) Trop. Med. Parasitol. 41. 297–298.
Stein, et al., J. of Clinical Microbiology, 30:2462–2499 (Sep. 1992). "Detection of Coxiella burnetii by DNA Amp. Using Polymerase Chain Reaction".
Zhang, et al., Molecular Microbiology 5(2):381–391 (1991), "Genetic Analysis of Superoxide Dismutase, the 23 kD Antigen of Mycobacterium tuberculosis".
Thangaraj, et al., Nuc. Acids Res., 17:8378 (1989), "Nucleotide and deduced Amino Acid Sequence of Mycobacterium leprae manganese superoxide dismutase".

Primary Examiner—W. Gary Jones
Assistant Examiner—Lisa Arthur
Attorney, Agent, or Firm—George M. Gould; William H. Epstein; Raina Semionow

[57] ABSTRACT

The use of the superoxide dismutase (SOD) gene system as a target for the detection and differentiation of pathogenic and non-pathogenic organisms including bacteria, fungi and protozoans is described. Also described are oligonucleotides which may be used in the form of primers and probes to amplify and detect target sequences derived from SOD genes, especially from SOD genes of pathogenic and non-pathogenic organisms.

35 Claims, 2 Drawing Sheets

Fig. 1 POSITION AND ORIENTATION OF PRIMERS USED FOR SEQUENCING CLONED SOD - AMPLICONS

Hybridization with Probe specific for M. intracellulare

Mycobacteria

SEQUENCE LISTING ( 1 ) GENERAL INFORMATION:

( i i i ) NUMBER OF SEQUENCES: 44

( 2 ) INFORMATION FOR SEQ ID NO: 1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO: 1:

AGCTTCACCA CAGCAAGCAC CA            22

( 2 ) INFORMATION FOR SEQ ID NO: 2:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO: 2:

TCGKCCCAGT TCACGACRTT CCA            23

( 2 ) INFORMATION FOR SEQ ID NO: 3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO: 3:

CCAARCTCGA AGAGGCGCGS GCCAA            25

( 2 ) INFORMATION FOR SEQ ID NO: 4:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO: 4:

GACAAGCCSA CSGGHGANYT SGCCGCVGCS ATCGMYG        37

( 2 ) INFORMATION FOR SEQ ID NO: 5:

( i ) SEQUENCE CHARACTERISTICS:
        ( A ) LENGTH: 37 base pairs
        ( B ) TYPE: nucleic acid ( C ) STRANDEDNESS: single
( D ) TOPOLOGY: linear ( i i ) MOLECULE TYPE: other nucleic acid ( x i ) SEQUENCE DESCRIPTION: SEQ ID NO: 5:

GACAAGCCCA CCGGCGAACT CGCCGCAGCC ATCGCCG 37

( 2 ) INFORMATION FOR SEQ ID NO: 6:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO: 6:

GACAAGCCGA CCGGCGAATT GGCCGCCGCS ATCGACG 37

( 2 ) INFORMATION FOR SEQ ID NO: 7:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO: 7:

GACAAGCCCA CCGGTGAGCT GGCCGCCGCG ATCGACG 37

( 2 ) INFORMATION FOR SEQ ID NO: 8:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO: 8:

GACAAGCCGA CCGGTGACCT GGCCGCCGCG ATCGACG 37

( 2 ) INFORMATION FOR SEQ ID NO: 9:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO: 9:

GACAAGCCGA CGGGCGATCT GGCCGCGGCG ATCGACG 37

( 2 ) INFORMATION FOR SEQ ID NO: 10:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO: 10:

GACAAGCCGA CCGGAGAACT GGCCGCCGCG ATCGATG 37

( 2 ) INFORMATION FOR SEQ ID NO: 11:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO: 11:

GACAAGCCGA CCGGAGATCT CGCCGCCGCC ATCGACG 37

( 2 ) INFORMATION FOR SEQ ID NO: 12:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO: 12:

GACAAGCCGA CCGGCGAACT CGCCGCGGCC ATCGACG 37

( 2 ) INFORMATION FOR SEQ ID NO: 13:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO: 13:

CCTTCGGATC CTTCGACCGG TTCCGCGCGC AGTTCAG 37

( 2 ) INFORMATION FOR SEQ ID NO: 14:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO: 14:

GTCCTTCGAC AAGTTCCGAG CGCAATTCAG CGCCGCC 37

( 2 ) INFORMATION FOR SEQ ID NO: 15:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO: 15:

TCTGGGCGGC CGGTTGCTCA CCTTT 25

(2) INFORMATION FOR SEQ ID NO: 16:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 16:

GTCCCCGAAC GGCGGAGACA AGCCGACCGG AGATCTC     37

(2) INFORMATION FOR SEQ ID NO: 17:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 17:

GCTAGGCATT GTTCCGCTGC TGCTGC     26

(2) INFORMATION FOR SEQ ID NO: 18:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 18:

TCCGCGATCG TCGGGCATGA GAAGGCCCTC GCGTTCA     37

(2) INFORMATION FOR SEQ ID NO: 19:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 19:

CCAGACGAAC TTTCCACTCG GA     22

(2) INFORMATION FOR SEQ ID NO: 20:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 20:

TGACACACTC GGCAGCAGGC TGCTCACCTT CCAGCTT     37

(2) INFORMATION FOR SEQ ID NO: 21:

(i) SEQUENCE CHARACTERISTICS:
        (A) LENGTH: 22 base pairs
        (B) TYPE: nucleic acid ( C ) STRANDEDNESS: single
            ( D ) TOPOLOGY: linear ( i i ) MOLECULE TYPE: other nucleic acid ( x i ) SEQUENCE DESCRIPTION: SEQ ID NO: 21:

ACGACAGCCT GGGCGATCGG CT                                                    22

( 2 ) INFORMATION FOR SEQ ID NO: 22:

( i ) SEQUENCE CHARACTERISTICS:
            ( A ) LENGTH: 37 base pairs
            ( B ) TYPE: nucleic acid
            ( C ) STRANDEDNESS: single
            ( D ) TOPOLOGY: linear ( i i ) MOLECULE TYPE: other nucleic acid ( x i ) SEQUENCE DESCRIPTION: SEQ ID NO: 22:

ACGAACTTCC CGCTAGGCAT TGTTCCGCTG CTGCTGC                                    37

( 2 ) INFORMATION FOR SEQ ID NO: 23:

( i ) SEQUENCE CHARACTERISTICS:
            ( A ) LENGTH: 22 base pairs
            ( B ) TYPE: nucleic acid
            ( C ) STRANDEDNESS: single
            ( D ) TOPOLOGY: linear ( i i ) MOLECULE TYPE: other nucleic acid ( x i ) SEQUENCE DESCRIPTION: SEQ ID NO: 23:

AGTCGACTTT GCCAAGGCGT TT                                                    22

( 2 ) INFORMATION FOR SEQ ID NO: 24:

( i ) SEQUENCE CHARACTERISTICS:
            ( A ) LENGTH: 23 base pairs
            ( B ) TYPE: nucleic acid
            ( C ) STRANDEDNESS: single
            ( D ) TOPOLOGY: linear ( i i ) MOLECULE TYPE: other nucleic acid ( x i ) SEQUENCE DESCRIPTION: SEQ ID NO: 24:

CACWCSATCT GGTGGAAGAA CCT                                                   23

( 2 ) INFORMATION FOR SEQ ID NO: 25:

( i ) SEQUENCE CHARACTERISTICS:
            ( A ) LENGTH: 22 base pairs
            ( B ) TYPE: nucleic acid
            ( C ) STRANDEDNESS: single
            ( D ) TOPOLOGY: linear ( i i ) MOLECULE TYPE: other nucleic acid ( x i ) SEQUENCE DESCRIPTION: SEQ ID NO: 25:

ACGGYGGYGA CAAGCCGACC GG                                                    22

( 2 ) INFORMATION FOR SEQ ID NO: 26:

( i ) SEQUENCE CHARACTERISTICS:
            ( A ) LENGTH: 22 base pairs
            ( B ) TYPE: nucleic acid
            ( C ) STRANDEDNESS: single
            ( D ) TOPOLOGY: linear ( i i ) MOLECULE TYPE: other nucleic acid ( x i ) SEQUENCE DESCRIPTION: SEQ ID NO: 26:

GTCTGSTGGT CGTARASCTG GA                                22

( 2 ) INFORMATION FOR SEQ ID NO: 27:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO: 27:

GGATTTGGCT TTCAACTTGG G                                 21

( 2 ) INFORMATION FOR SEQ ID NO: 28:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO: 28:

GGCGAGCCAA CCGGCGCTTT GG                                22

( 2 ) INFORMATION FOR SEQ ID NO: 29:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO: 29:

GAAGAACCTG AGCCTTAACG GT                                22

( 2 ) INFORMATION FOR SEQ ID NO: 30:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO: 30:

GAGCCAACCG GTGAGCTAGC C                                 21

( 2 ) INFORMATION FOR SEQ ID NO: 31:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO: 31:

GAAGAACCTC TCCCCCAACG GC                                22

( 2 ) INFORMATION FOR SEQ ID NO: 32:

( i ) SEQUENCE CHARACTERISTICS:
    ( A ) LENGTH: 491 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Mycobacterium tuberculosis/SOD gene ( x i ) SEQUENCE DESCRIPTION: SEQ ID NO: 32:

| | | | | | | |
|---|---|---|---|---|---|---|
| AGCTTCACCA | CAGCAAGCAC | CACGCCACCT | ACGTAAAGGG | CGCCAATGAC | GCCGTCGCCA | 60 |
| AACTCGAAGA | GGCGCGCGCC | AAGGAAGATC | ACTCAGCGAT | CTTGCTGAAC | GAAAAGAATC | 120 |
| TAGCTTTCAA | CCTCGCCGGC | CACGTCAATC | ACACCATCTG | GTGGAAGAAC | CTGTCGCCTA | 180 |
| ACGGTGGTGA | CAAGCCCACC | GGCGAACTCG | CCGCAGCCAT | CGCCGACGCG | TTCGGTTCGT | 240 |
| TCGACAAGTT | CCGTGCGCAG | TTCCACGCGG | CCGCTACCAC | CGTGCAGGGG | TCGGGCTGGG | 300 |
| CGGCACTGGG | CTGGGACACA | CTCGGCAACA | AGCTGCTGAT | ATTCCAGGTT | TACGACCACC | 360 |
| AGACGAACTT | CCCGCTAGGC | ATTGTTCCGC | TGCTGCTGCT | CGACATGTGG | GAACACGCCT | 420 |
| TCTACCTGCA | GTACAAGAAC | GTCAAAGTCG | ACTTTGCCAA | GGCGTTTTGG | AACGTCGTGA | 480 |
| ACTGGGCCGA | T | | | | | 491 |

( 2 ) INFORMATION FOR SEQ ID NO: 33:

( i ) SEQUENCE CHARACTERISTICS:
    ( A ) LENGTH: 491 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Mycobacterium avium/SOD gene ( x i ) SEQUENCE DESCRIPTION: SEQ ID NO: 33:

| | | | | | | |
|---|---|---|---|---|---|---|
| AGCTTCACCA | CAGCAAGCAC | CACGCCACCT | ACGTCAAAGG | CGTGAACGAC | GCTCTTGCCA | 60 |
| AGCTCGAAGA | GGCCCGCGCC | AACGAGGACC | ACGCTGCGAT | CTTCCTGAAC | GAAAAGAACC | 120 |
| TCGCCTTCCA | CCTGGGCGGC | CACGTCAACC | ACTCGATCTG | GTGGAAGAAC | CTGTCGCCGG | 180 |
| ACGGCGGTGA | CAAGCCCACC | GGTGAGCTGG | CCGCCGCGAT | CGACGACGCG | TTCGGGTCCT | 240 |
| TCGACAAGTT | CCGAGCGCAA | TTCAGCGCCG | CCGCCAACGG | CCTGCAGGGC | TCCGGCTGGG | 300 |
| CGGTGCTGGG | CTATGACACC | CTGGGCAGCC | GGTTGCTGAC | CTTCCAGCTC | TACGACCAGC | 360 |
| GGGCCAACGT | CCCGCTGGGC | ATCATCCCGC | TTCTGCAGGT | CGACATGTGG | GAGCACGCGT | 420 |
| TCTACCTGCA | GTACAAGAAC | GTCAAGGCGG | ACTACGTCAA | GGCGTTCTGG | AACGTCGTGA | 480 |
| ACTGGGCCGA | T | | | | | 491 |

( 2 ) INFORMATION FOR SEQ ID NO: 34:

( i ) SEQUENCE CHARACTERISTICS:
    ( A ) LENGTH: 491 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Mycobacterium intracellulare/SOD gene ( x i ) SEQUENCE DESCRIPTION: SEQ ID NO: 34:

| | | | | | | |
|---|---|---|---|---|---|---|
| AGCTTCACCA | CAGCAAGCAC | CACGCCACCT | ACGTCAAAGG | CGTGAACGAC | GCTCTGTCCA | 60 |
| AGCTCGAAGA | GGCCCGTGCC | AACGAAGATC | ACGCTGCGAT | CTTCCTGAAC | GAAAAGAACC | 120 |
| TGGCCTTTCA | CCTGGGCGGC | CACGTCAACC | ACTCCATCTG | GTGGAAGAAC | CTGTCGCCGG | 180 |
| ACGGCGGCGA | CAAGCCGACC | GGCGAATTGG | CCGCCGCGAT | CGACGACGCC | TTCGGATCCT | 240 |
| TCGACCGGTT | CCGCGCGCAG | TTCAGCGCGG | CCGCCAACGG | CCTGCAGGGG | TCGGGCTGGG | 300 |
| CGGTGCTGGG | CTACGACACC | CTCGGCAACC | GGCTGCTGAC | CTTCCAGCTC | TACGACCAGC | 360 |
| AGGCCAACGT | GCCGCTGGGC | ATCATTCCGC | TGCTGCAGGT | CGACATGTGG | GAGCACGCTT | 420 |
| TCTACCTGCA | GTACAAGAAC | GTCAAGGCGG | ACTACGTCAA | GGCGTTCTGG | AACGTCGTGA | 480 |
| ACTGGGACGA | T | | | | | 491 |

( 2 ) INFORMATION FOR SEQ ID NO: 35:

( i ) SEQUENCE CHARACTERISTICS:
        ( A ) LENGTH: 491 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( B ) STRAIN: Mycobacterium scrofulaceum/SOD gene ( x i ) SEQUENCE DESCRIPTION: SEQ ID NO: 35:

| | | | | | | |
|---|---|---|---|---|---|---|
| AGCTTCACCA | CAGCAAGCAC | CACGCCACGT | ACGTCAAGGG | CGTGAACGAC | GCCGTCGCCA | 60 |
| AACTCCAAGA | GGCACGCGCC | AATGACGACC | ACGCCGCGAT | CTTCCTGAAC | GAAAAGAACC | 120 |
| TGGCGTTCCA | CCTCGGCGGC | CACGTGAACC | ACTCGATCTG | GTGGAAGAAC | CTCTCGCCGG | 180 |
| ACGGCGGCGA | CAAGCCGACC | GGAGAACTGG | CCGCCGCGAT | CGATGACGCG | TTCGGATCGT | 240 |
| TCGACAAATT | CCGCGCCCAG | TTCAGTGCGG | CCGCCAACGG | CCTGCAGGGT | TCGGGCTGGG | 300 |
| CGGTGCTGGG | CTATGACACA | CTCGGCAGCA | GGCTGCTCAC | CTTCCAGCTT | TACGACCAGC | 360 |
| AGGCCAACGT | CCCGCTCGGC | ATCATTCCGC | TGCTGCAGGT | CGACATGTGG | GAGCACGCCT | 420 |
| TTTACTTGCA | GTACAAGAAC | GTCAAGGCCG | ACTACGTCAA | GGCCTTCTGG | AATGTCGTGA | 480 |
| ACTGGGCCGA | G | | | | | 491 |

( 2 ) INFORMATION FOR SEQ ID NO: 36:

( i ) SEQUENCE CHARACTERISTICS:
        ( A ) LENGTH: 491 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Mycobacterium kansasii/SOD gene ( x i ) SEQUENCE DESCRIPTION: SEQ ID NO: 36:

| | | | | | | |
|---|---|---|---|---|---|---|
| AGCTTCACCA | CAGCAAGCAC | CACGCCACCT | ACGTCAAGGG | CGCCAACGAT | GCGGTCGCCA | 60 |
| AACTCGAAGA | GGCGCGCGCC | AAGGAAGACC | ACTCGGCGAT | CTTGCTGAAC | GAGAAGAACT | 120 |
| TGGCCTTCAA | CCTCGCCGGC | CACGTCAACC | ACACGATCTG | GTGGAAGAAC | CTTTCTCCCA | 180 |
| ACGGAGGCGA | CAAGCCGACC | GGCGAACTCG | CCGCGGCCAT | CGACGAGGCG | TTCGGGTCCT | 240 |
| TCGACAAGTT | TCGTGCCCAA | TTCCACGCCG | CCGCCACCAC | GGTGCAGGGG | TCGGGCTGGG | 300 |

| | | | | | | |
|---|---|---|---|---|---|---|
| CGGCGCTGGG | CTGGGACACT | CTCGGCAACA | AGCTGCTGAT | ATTCCAGGTC | TACGACCACC | 360 |
| AGACGAACTT | TCCACTCGGA | ATCATTCCGT | TACTGCTGCT | CGACATGTGG | GAACACGCTT | 420 |
| TCTACCTCCA | GTACAAGAAT | GTCAAGGTCG | ACTTCGCCAA | AGCATTCTGG | AACGTCGTGA | 480 |
| ACTGGGACGA | T | | | | | 491 |

( 2 ) INFORMATION FOR SEQ ID NO: 37:

( i ) SEQUENCE CHARACTERISTICS:
        ( A ) LENGTH: 491 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Mycobacterium fortuitum/SOD gene ( x i ) SEQUENCE DESCRIPTION: SEQ ID NO: 37:

| | | | | | | |
|---|---|---|---|---|---|---|
| AGCTTCACCA | CAGCAAGCAC | CACGCCGCGT | ACGTCAAGGG | CGTCAACGAC | GCCGTGGCCA | 60 |
| AGCTCGATGA | GGCGCGGGCC | AACGGTGACC | ACGCGGCGAT | CTTCCTCAAC | GAGAAGAACC | 120 |
| TGGCGTTCCA | TCTCGGCGGC | CACGTGAACC | ACTCGATCTG | GTGGAAGAAC | CTGTCCCCCA | 180 |
| ACGGTGGTGA | CAAGCCGACG | GGCGATCTGG | CCGCGGCGAT | CGACGATCAG | TTCGGCTCGT | 240 |
| TCGACAAGTT | CCAGGCGCAG | TTCACCGCCG | CCGCCAACGG | GCTGCAGGGC | TCGGGCTGGG | 300 |
| CCGTGCTCGG | CTACGACAGC | CTGGGCGATC | GGCTGCTGAC | CTTCCAGCTC | TACGACCAGC | 360 |
| AGGCCAACGT | GCCGCTCGGC | ATCATCCCGC | TGCTCCAGGT | CGACATGTGG | GAGCACGCCT | 420 |
| TCTACCTGCA | GTACAAGAAC | GTCAAGGCCG | ACTACGTCAA | GGCGTTCTGG | AAAGTCGTGA | 480 |
| ACTGGGACGA | T | | | | | 491 |

( 2 ) INFORMATION FOR SEQ ID NO: 38:

( i ) SEQUENCE CHARACTERISTICS:
        ( A ) LENGTH: 491 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Mycobacterium simiae/SOD gene ( x i ) SEQUENCE DESCRIPTION: SEQ ID NO: 38:

| | | | | | | |
|---|---|---|---|---|---|---|
| AGCTTCACCA | CAGCAAGCAC | CATGCGACGT | ACGTCAAGGG | TTTGAACGAC | GCCATTGCCA | 60 |
| AGCTTGAAGA | GGCGCGGGCC | AACGACGACC | ATGCCGCGAT | CTTCTTGAAC | GAGAAGAATC | 120 |
| TGGCATTCCA | CCTCGGTGGC | CACGTCAACC | ACTCCATCTG | GTGGAAAAAC | CTGTCCCCGA | 180 |
| ACGGCGGAGA | CAAGCCGACC | GGAGATCTCG | CCGCCGCCAT | CGACGACGCC | TTCGGTTCGT | 240 |
| TCGACAAGTT | CCGCGCACAG | TTCAGCGCCG | CCGCCAACGG | CTTGCAGGGC | TCGGGCTGGG | 300 |
| CGGTACTCGG | CTACGACACC | CGGGGCGACC | GACTGCTGAC | CTTCCAGCTT | TACGACCAGC | 360 |
| AGGCCAACGT | CCCGCTGGGC | ATCATCCCGC | TGCTGCAGGT | CGACATGTGG | GAGCACGCCT | 420 |
| TCTACCTGCA | GTACAAGAAC | GTCAAGGCGG | ACTACGTCAA | GGCGTTCTGG | AACGTCGTGA | 480 |
| ACTGGGACGA | T | | | | | 491 |

( 2 ) INFORMATION FOR SEQ ID NO: 39:

( i ) SEQUENCE CHARACTERISTICS:
  ( A ) LENGTH: 491 base pairs
  ( B ) TYPE: nucleic acid
  ( C ) STRANDEDNESS: single
  ( D ) TOPOLOGY: linear ( i i ) MOLECULE TYPE: cDNA ( v i ) ORIGINAL SOURCE:
  ( A ) ORGANISM: Mycobacterium gordonae/SOD gene ( x i ) SEQUENCE DESCRIPTION: SEQ ID NO: 39:

| | | | | | | |
|---|---|---|---|---|---|---|
| AGCTTCACCA | CAGCAAGCAC | CACGCCACCT | ACGTCAAAGG | CGTCAACGAC | GCGGTCGCCA | 60 |
| AGCTGGAAGA | AGCGCGCGCC | AAAGGCGACC | ACTCGGCCAT | CTTTTTGAAC | GAGAAGAACC | 120 |
| TGGCCTTCCA | CCTGGGCGGT | CACGTCAACC | ACTCCATCTG | GTGGAAGAAC | CTGTCGCCGG | 180 |
| ACGGCGGCGA | CAAGCCGACC | GGTGACCTGG | CCGCCGCGAT | CGACGACCAG | TTCGGCTCGT | 240 |
| TCGACAAGTT | CCAGGCTCAG | TTCAGCGCCG | CCGCAAACGG | CCTACAGGGC | TCGGGCTGGG | 300 |
| CGGTGCTCGG | CTACGACACT | CTGGGCGGCC | GGTTGCTCAC | CTTTCAGCTC | TACGACCAGC | 360 |
| AGGCCAATGT | CCCGCTCGGT | GTCATTCCGC | TGTTGCAGGT | CGACATGTGG | GAGCACGCCT | 420 |
| TCTACCTGCA | GTACAAGAAC | GTCAAGGCCG | ACTACGTCAA | GGCCTTCTGG | AACGTCGTGA | 480 |
| ACTGGGACGA | C | | | | | 491 |

( 2 ) INFORMATION FOR SEQ ID NO: 40:

( i ) SEQUENCE CHARACTERISTICS:
  ( A ) LENGTH: 491 base pairs
  ( B ) TYPE: nucleic acid
  ( C ) STRANDEDNESS: single
  ( D ) TOPOLOGY: linear ( i i ) MOLECULE TYPE: cDNA ( v i ) ORIGINAL SOURCE:
  ( A ) ORGANISM: Mycobacterium xenopi/SOD gene ( x i ) SEQUENCE DESCRIPTION: SEQ ID NO: 40:

| | | | | | | |
|---|---|---|---|---|---|---|
| AGCTTCACCA | CAGCAAGCAC | CACGCGACGT | ACGTCAAAGG | CGCCAACGAC | GCGCTCGCCA | 60 |
| AGCTGGAGGA | GGCGCGCGCC | AAAGACGATC | ATTCCGCGAT | CGTCGGGCAT | GAGAAGGCCC | 120 |
| TCGCGTTCAA | CCTGGCCGGC | CATGTCAATC | ACTGCCTGTG | GTGGAAGAAC | CTGTCCCCCA | 180 |
| ACGGCGGTGA | CAAGCCGACC | GGCGAATTGG | CCGCCGCCAT | CGACGACGCG | TTCGGCTCGT | 240 |
| TCGACAAGTT | CCGCGCCCAG | TTCACCGCGG | CCGCCACGAC | CGTGCAGGGG | TCGGGCTGGG | 300 |
| CGGCACTCGG | CTGGACAGC | CTGGGTGGCA | AGCTCCTGGT | GTTCCAGGTC | TACGACCACC | 360 |
| AGTCCAACTT | CCCGCTCGGG | ATCGTCCCCC | TGCTGGTGCT | CGACATGTGG | GAGCACGCCT | 420 |
| TCTACCTGCA | GTACAAGAAT | GTCAAGGCTG | ACTTCGCCAA | AGCATTCTGG | AACGTCGTGA | 480 |
| ACTGGGCCGA | T | | | | | 491 |

( 2 ) INFORMATION FOR SEQ ID NO: 41:

( i ) SEQUENCE CHARACTERISTICS:
  ( A ) LENGTH: 495 base pairs
  ( B ) TYPE: nucleic acid
  ( C ) STRANDEDNESS: single
  ( D ) TOPOLOGY: linear ( i i ) MOLECULE TYPE: cDNA ( v i ) ORIGINAL SOURCE:
  ( A ) ORGANISM: Corynebacterium diphteriae/SOD gene ( x i ) SEQUENCE DESCRIPTION: SEQ ID NO: 41:

| | | | | | | |
|---|---|---|---|---|---|---|
| AGCTTCACCA | CAGCAAGCAC | CACGCTAACT | ACGTGAACGG | TGCAAATACT | GCTCTTGAGA | 60 |
| AGCTGCAAAA | GGCTCGCGAG | AACGGTGAGA | TCGGTGCTGT | TGTCACCGCT | TTGTCCAAGG | 120 |
| ATTTGGCTTT | CAACTTGGGT | GGCCACACCA | ACCACTCCAT | CTTCTGGAAG | AACCTCTCCC | 180 |
| CTAACGGTGG | CGGCGAGCCA | ACCGGCGCTT | TGGCTGAGGC | AATTGCCAAG | GAGTTCGGTT | 240 |
| CTTTTGAGAA | GTTCAAGGAT | CACTTCTCTG | CTGCGGCTCT | TGGTCTGCAG | GGTTCCGGCT | 300 |
| GGGCTGTTCT | CGGCTACGAT | CACATCGGTG | CCGTCTGGT | TATCGAGCAG | CTCACTGACC | 360 |
| AGCAGGGCAA | CATCTCCGCT | AACCTGACCC | CACTTCTTAT | GCTCGATATG | TGGGAGCACG | 420 |
| CTTTCTACCT | TCAGTACAAG | AACGTGAAGG | CTGACTACGT | CAAGGCTGTG | TGGAACGTCG | 480 |
| TGAACTGGGA | CGATG | | | | | 495 |

( 2 ) INFORMATION FOR SEQ ID NO: 42:

( i ) SEQUENCE CHARACTERISTICS:
            ( A ) LENGTH: 491 base pairs
            ( B ) TYPE: nucleic acid
            ( C ) STRANDEDNESS: single
            ( D ) TOPOLOGY: linear ( i i ) MOLECULE TYPE: cDNA ( v i ) ORIGINAL SOURCE:
            ( A ) ORGANISM: C. pseudodiphteriticum/SOD gene ( x i ) SEQUENCE DESCRIPTION: SEQ ID NO: 42:

| | | | | | | |
|---|---|---|---|---|---|---|
| AGCTTCACCA | CAGCAAGCAC | CACAACACTT | ACGTGCAGGG | TGCTAACGCA | GCTTTGGACG | 60 |
| CTCTGGAAGA | AGAGCGCAAC | GGCGAAGCCA | ACCCAGACCG | CATCCGTGCG | CTGTCCAAGA | 120 |
| ACTTGGCTTT | CCAACCTGGC | CACACCAACC | ACTCCATCTT | CTGGAAGAAC | CTGAGCCCTA | 180 |
| ACGGTGGCGG | CGAGCCAACC | GGTGAGCTAG | CAGAGGCTAT | CGACCGCGAC | TTTGGTTCCT | 240 |
| TCGAGAAGTT | CAAGGCGCAC | TTCTCCGCAG | CAGCACTCGG | CCTGCAGGGT | TCCGGCTGGG | 300 |
| CCGTGCTGGG | TTACGACCAC | ATTGCTGGTC | GCCTGCTCGT | TGAGCAGCTG | ACCGACCAGC | 360 |
| AGGGCAACAC | TTCCGTGAAC | TTCACCCCAC | TGCTGATGCT | GGATATGTGG | GAGCACGCTT | 420 |
| TCTACCTGCA | GTACAAGAAC | GTCAAGCCTG | ATTACGTCAA | GGCTGTCTGG | AACGTCGTGA | 480 |
| ACTGGGACGA | T | | | | | 491 |

( 2 ) INFORMATION FOR SEQ ID NO: 43:

( i ) SEQUENCE CHARACTERISTICS:
            ( A ) LENGTH: 490 base pairs
            ( B ) TYPE: nucleic acid
            ( C ) STRANDEDNESS: single
            ( D ) TOPOLOGY: linear ( i i ) MOLECULE TYPE: cDNA ( v i ) ORIGINAL SOURCE:
            ( A ) ORGANISM: Nocardia asteroides/SOD gene ( x i ) SEQUENCE DESCRIPTION: SEQ ID NO: 43:

| | | | | | | |
|---|---|---|---|---|---|---|
| AGCTTCACCA | CAGCAAGCAC | CACGCCGCCT | ACGTCGCCGG | TGCCAACACG | GCACTGGAGA | 60 |
| AGCTGGAAGC | CGCCCGTGAG | GCCGGCGATC | ACAGCGCGAT | CTTCCTGCAC | GAGAAGAACC | 120 |
| TCGCGTTCCA | CCTCGGCGGA | CACGTCAACC | ACTCCATCTG | GTGGAAGAAC | CTGTCCCCCA | 180 |
| ACGGTGGCGA | CAAGCCGGTC | GGCGAGCTGG | CCGCGGCCAT | CGACGACCAG | TTCGGTTCGT | 240 |
| TCGACAAGTT | CCGCGCGCAG | TTCACCGCCG | CGCCAACGGC | CTGCAGGGCT | CGGGCTGGGC | 300 |
| GGTGCTCGGT | TACGACACCC | TCGGCCAGAA | GCTGCTGACC | TTCCAGCTCT | ACGACCAGCA | 360 |

| | | | | | | |
|---|---|---|---|---|---|---|
| GGCCAACGTG | CCGCTGGGCA | TCATCCCGCT | GCTCCAAGTC | GACATGTGGG | AGCACGCCTT | 420 |
| CTACCTGCAG | TACAAGAACG | TCAAGGCCGA | CTACGTGACC | GCGTTGTGGA | ACGTCGTGCA | 480 |
| CTGGGCCGAT | | | | | | 490 |

( 2 ) INFORMATION FOR SEQ ID NO: 44:

( i ) SEQUENCE CHARACTERISTICS:
    ( A ) LENGTH: 491 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Actinomyces viscosus/SOD gene ( x i ) SEQUENCE DESCRIPTION: SEQ ID NO: 44:

| | | | | | | |
|---|---|---|---|---|---|---|
| AGCTTCACCA | CAGCAAGCAC | CACGCCGCCT | ACGTCGCTGG | CGCCAACGCC | GCCCTGGAGG | 60 |
| CCCTCGCCGC | CGCCCGCGAG | GACGGCGACC | TGGGTGCGAT | CAACCTGTGG | GAGAAGAACC | 120 |
| TCGCCTTCAA | CCTGGGCGGC | CACACCAACC | ACTCCGTGTT | CTGGAAGAAC | CTCTCCCCA | 180 |
| ACGGCGGCGG | CCAGCCCGAG | GGCGAGCTCG | CCGAGGCCAT | CAAGGACTCC | TTCGGCTCCT | 240 |
| TCGAGAAGTT | CCAGGCGCAG | TTCACCGCCA | CCGCCCTGGG | CATCCAGGGC | TCGGGCTGGG | 300 |
| CCGTGCTCGC | CTACGACTCA | ATCTCCGGCA | AGCTGCTGAT | CTTCCAGCTC | TTCGACCAGC | 360 |
| AGGCCAACGT | GCCCGTGGGC | ACGACCCCGC | TGTTCATGGT | GGACATGTGG | GAGCACGCAT | 420 |
| TCTACCTCGA | CTACCTCAAC | GTCAAGGCCG | ACTACGTCAA | GGCCATCTGG | AACGTCGTGA | 480 |
| ACTGGGACGA | T | | | | | 491 |

METHOD AND REAGENTS FOR DETECTION OF MYCOBACTERIA USING SUPEROXIDE DISMUTASE GENE TARGETING

FIELD OF THE INVENTION

The inventions described and claimed herein relate to the use of the superoxide dismutase (SOD) gene system as a target for the detection and differentiation of pathogenic and non-pathogenic organisms. More specifically, the invention relates to oligonucleotides derived from the SOD gene family which may be used in the form of primers and probes.

BACKGROUND OF THE INVENTION

SOD is an enzyme which catalyzes the dismutation of free superoxide ($O_2^-$) to give molecular oxygen and hydrogen peroxide as follows:

$$2\ O_2^- + 2H^+ \rightarrow O_2 + H_2O_2.$$

The resulting peroxide is then converted by catalases or peroxidases into $H_2O$. Superoxide ($O_2^-$) is a toxic by-product of aerobic respiration and reacts with peroxide ($O_2^{2-}$) to cause damage to proteins, lipids and nucleic acids. The enzyme superoxide dismutase (SOD) counteracts the toxic effects of the radicals by conversion of superoxide to molecular oxygen and peroxide.

The term "polymerase chain reaction" or "PCR" refers to a process of amplifying one or more specific nucleic acid sequences, wherein (1) oligonucleotide primers which determine the ends of the sequences to be amplified are annealed to single-stranded nucleic acids in a test sample, (2) a nucleic acid polymerase extends the 3'-ends of the annealed primers to create a nucleic acid strand complementary in sequence to the nucleic acid to which the primers were annealed, (3) the resulting double-stranded nucleic acid is denatured to yield two single-stranded nucleic acids, and (4) the processes of primer annealing, primer extension and product denaturation are repeated enough times to generate easily identified and measured amounts of the sequences defined by the primers. Practical control of the sequential annealing, extension and denaturation steps is exerted by varying the temperature of the reaction container, normally in a repeating cyclical manner. Annealing and extension occur optimally in the 37° C.–80° C. temperature range (exact value depending on primer concentrations and sequences), whereas denaturation requires temperatures in the 80°–100° C. range (exact value depending on target sequence and concentration).

The term "oligonucleotide" refers to a single-stranded nucleic acid comprised of two or more deoxyribonucleotides, such as primers, probes, nucleic acid fragments to be detected and nucleic acid controls. The exact size of an oligonucleotide depends on many factors and the ultimate function or use of the oligonucleotide. Oligonucleotides can be prepared by any suitable method, including, for example, cloning and restriction of appropriate sequences and direct chemical synthesis by a method such as the phosphotriester method of Narang et al., Meth. Enzymol. 68, 90–99 (1979); the phosphodiester method of Brown et al., Meth. Enzymol. 68, 109–151 (1979); the diethylphosphoramidite method of Beaucage et al., Tetrahedron Lett. 22, 1859–1862 (1981); and the solid support method described in the U.S. Pat. No. 4,458,066.

The term "primer" refers to an oligonucleotide, whether natural or synthetic, capable of acting as a point of initiation of DNA synthesis under conditions in which synthesis of a primer extension product complementary to a nucleic acid strand is induced, i.e. in the presence of the different nucleoside triphosphates and an agent for polymerization (e.g. a DNA polymerase or a reverse transcriptase) in an appropriate buffer and at a suitable temperature. The appropriate length of a primer depends on the intended use of the primer but typically ranges from 15 to 40 nucleotides. Short primer molecules generally require lower temperatures to form sufficiently stable hybrid complexes with the template. A primer need not reflect the exact sequence of the template but must be sufficiently complementary to hybridize with a template and serve to initiate DNA synthesis under the chosen reaction conditions.

The term "primer" may refer to more than one primer, particularly in the case where there is some ambiguity in the information regarding one or both ends of the target region to be amplified. If a conserved region shows significant levels of polymorphism in a population, mixtures of primers can be prepared that will amplify such sequences, or the primers can be designed to amplify even mismatched sequences. A primer can be labeled, if desired, by incorporating a label detectable by radiometric, spectroscopic, photochemical, biochemical, immunochemical or chemical means. For example, useful labels include $^{32}P$, fluorescent dyes, electron-dense reagents, enzymes (as commonly used in ELISAs), biotin or haptens and proteins for which antisera or monoclonal antibodies are available. A label can also be used to "capture" the primer, so as to facilitate the immobilization of either the primer or a primer extension product, such as amplified DNA, on a solid support.

The term "probe" refers to an oligonucleotide containing a hybridizing sequence complementary to a part of the target sequence which may be labeled with a tag or attached to a solid support. Depending on the assay methods utilized for detecting hybrids formed between probes and nucleic acid sequences the probes may contain additional features in addition to the hybridizing region. In the dot blot format, for example, the probes are typically labeled. If the probe is first immobilized, as in the "reverse" dot blot format described below, the probe can also contain long stretches of poly-dT that can be fixed to a nylon support by irradiation, a technique described in more detail in PCT Patent Publication No. 89/11548. The appropriate length of a probe depends on the intended use of the probe but typically ranges from 15 to 40 nucleotides. Short probe molecules generally require lower temperatures to form sufficiently stable hybrid complexes with the target. A probe need not reflect the exact sequence of the template but must be sufficiently complementary to hybridize with the target sequence.

The probes of the present invention may be synthesized and labeled using the techniques described above for synthesizing oligonucleotides. For example, the probe may be labeled at the 5'-end with $^{32}P$ by incubating the probe with $^{32}P$-ATP and kinase. A suitable non-radioactive label for probes is horseradish peroxidase (HRP). Methods for preparing and detecting probes containing this label are described in U.S. Pat. Nos. 4,914,210 and 4,962,02. For additional information on the use of such labeled probes, see U.S. Pat. No. 4,789,630; Saiki et al., N. Eng. J. Med. 319, 537–541 (1988); and Bugawan et al., Bio/Technology 6, 943–947 (1988). Useful chromogens include red leuco dye and 3,3',5,5'-tetramethylbenzidine (TMB). Helmuth, PCR Protocols, San Diego, Calif., Academic Press, Inc., 1990, pp. 119–128, describes procedures for non-isotopic detection of PCR products.

SUMMARY OF THE INVENTION

The present invention relates to the use of the superoxide dismutase (SOD; EC 1.15.1.1) gene system as a target for the detection and differentiation of pathogenic and non-pathogenic organisms including bacteria, fungi and protozoans. In another aspect, the present invention relates to oligonucleotides derived from the SOD gene family. More particularly, it relates to oligonucleotides capable of hybridizing to a single-stranded nucleic acid sequence (target sequence) which is obtainable by amplifying and denaturing a part of a gene coding for a superoxide dismutase (SOD) using a polymerase chain reaction (PCR) and a pair of primers, the first primer containing the sequence 5'-AGC TTC ACC ACA GCA AGC ACC A-3'(SEQ ID NO: 1; Z205) as priming sequence and the second primer containing the sequence 5'-TCG KCC CAG TTC ACG ACR TTC CA-3'(SEQ ID NO: 2; Z212) as priming sequence.

These oligonucleotides may be used in the form of primers and probes to amplify and detect target sequences derived from SOD genes, especially, from SOD genes of pathogenic organisms including bacteria, fungi and protozoans. The primers and probes according to the present invention may also be used for amplifying and detecting target sequences derived from SOD genes of non-pathogenic organisms.

Objects of the present invention are the aforementioned oligonucleotides; primers and probes based on these oligonucleotides; methods, reagents and kits for the amplification and detection of target sequences derived from SOD genes and for the diagnosis of infections caused by procaryotic organisms; and the use of said oligonucleotides for the aforementioned purposes.

DETAILED DESCRIPTION OF THE INVENTION

Figure 1:
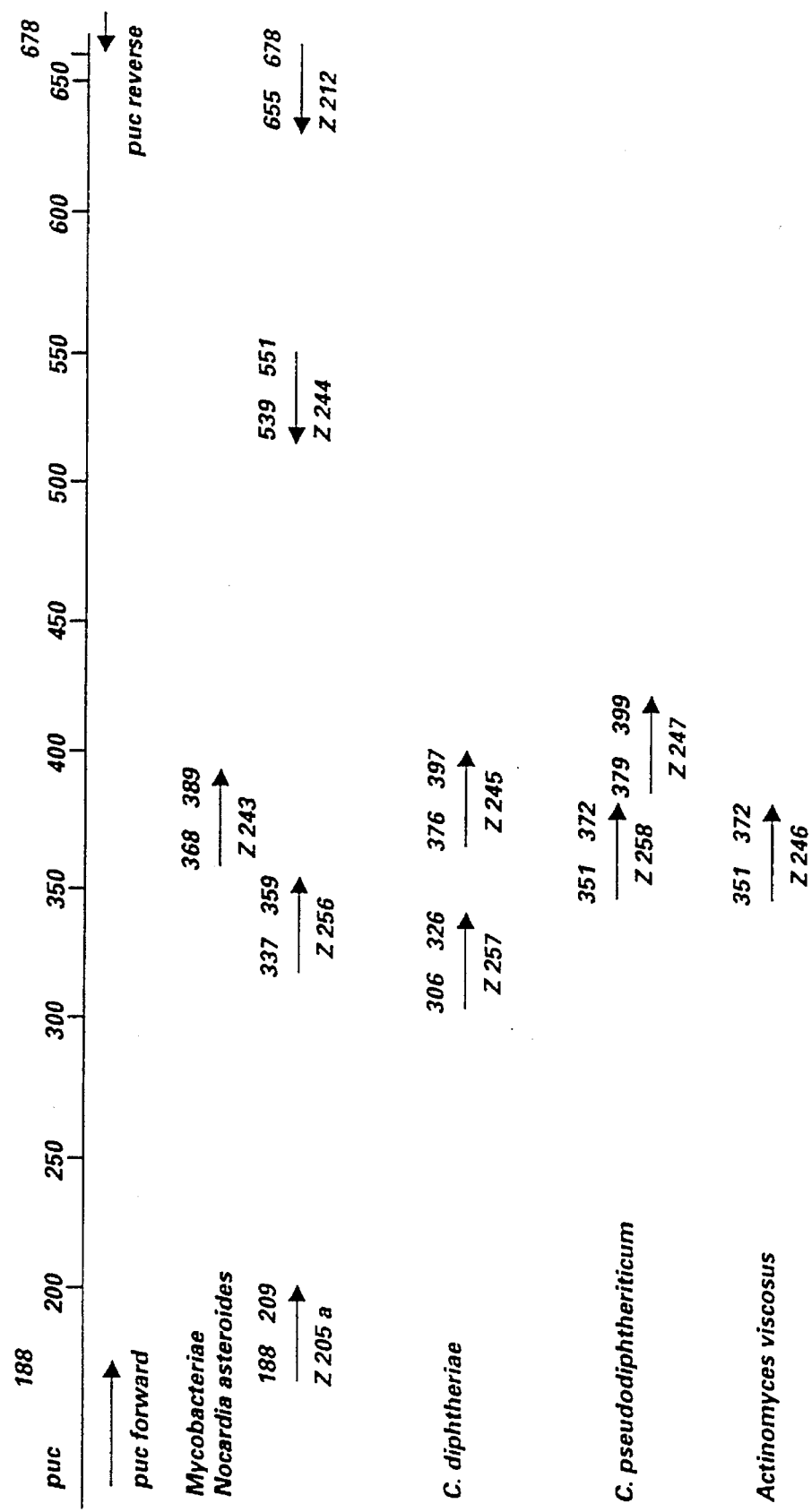
FIG. 1 shows the position of the sequencing primers within the SOD-gene.

Preferred oligonucleotides in accordance with the present invention are those which are capable of hybridizing to a region of the target sequence which is substantially conserved among the SOD genes of different organisms such as bacteria, fungi and protozoa (universal primers) or substantially conserved among the SOD genes of the different species belonging to a particular genus (genus specific oligonucleotides), and those which are capable of hybridizing to a region of the target sequence which is variable to a degree allowing differentiation among the SOD genes of the different species belonging to a particular genus (species specific oligonucleotides).

Oligonucleotides capable of hybridizing to a single-stranded nucleic acid sequence (target sequence) which is obtainable by amplifying a part of a gene coding for a superoxide dismutase (SOD) of a mycobacterial species using a polymerase chain reaction (PCR) and a pair of primers, the first primer containing the sequence of SEQ ID NO: 3 (Z261, cf. Table 17) as priming sequence and the second primer containing the sequence of SEQ ID NO: 2 (Z212) above as priming sequence are especially preferred. Among these, oligonucleotides capable of hybridizing to a region of the target sequence which is substantially conserved among the SOD genes of the different species belonging to the genus of mycobacteria (genus specific oligonucleotides), and oligonucleotides capable of hybridizing to a region of the target sequence which is variable to a degree allowing differentiation among the SOD genes of the different species belonging to the genus of mycobacteria (species specific oligonucleotides) are even more preferred.

As mentioned earlier, the oligonucleotides of the present invention may be used in the form of primers and probes to amplify and detect target sequences derived from SOD genes of pathogenic organisms including bacteria, fungi and protozoans and of non-pathogenic organisms. In a preferred aspect, the target nucleic acid is amplified by a PCR, using a pair of primers allowing amplification of a part of the SOD genes of the different species belonging to a particular genus. Genus detection may then be performed by mixing the amplified nucleic acid with genus specific probes and detecting if hybridization occurs, whereas species identification is carried out by determining the pattern of hybridization of the amplified nucleic acid to species specific probes.

In an especially preferred embodiment, the present invention relates to oligonucleotides which may be used in the form of primers and probes to amplify and detect target sequences derived from SOD genes of mycobacterial species, preferably of pathogenic mycobacterial species. The target nucleic acid is amplified by a PCR, using a pair of primers allowing amplification of a part of the SOD genes of the different mycobacterial species belonging to the genus of mycobacteria. Preferably, the pair of primers consist of a first primer comprising a priming sequence which is substantially homologous to the sequence of SEQ ID NO: 3 (Z261) and a second primer comprising a priming sequence which is substantially homologous to the sequence of SEQ ID NO: 2 (Z212). More preferably the pair of primers consist of a first primer comprising the sequence of SEQ ID NO: 3 (Z261) and a second primer comprising the sequence of SEQ ID NO: 2 (Z212) as priming sequence.

Genus detection may then be performed by mixing the amplified nucleic acid with genus specific probes comprising an oligonucleotide sequence of SEQ ID NO: 4 as hybridizing sequence, preferably a pool of probes comprising the oligonucleotide sequences of Z310–Z317 as hybridizing sequences (Table 18), and detecting if hybridization occurs. The species identification may be carried out by determining the pattern of hybridization of the amplified nucleic acid to species specific probes capable of hybridizing to a region of the target sequence which is variable to a degree allowing differentiation among the SOD genes of the different species belonging to the genus of mycobacteria.

Preferred species specific probes that may be utilized in accordance with the present invention are probes which contain a hybridizing sequence which is substantially homologous to the following sequences: 5'-CCT TCG GAT CCT TCG ACC GGT TCC GCG CGC ACT TCA G-3'(Z303, SEQ ID NO: 13) for *M. intracellulare;* 5'-GCT AGG CAT TGT TCC GCT GCT GCT GC-3'(Z336, SEQ ID NO: 17) and 5'-ACG AAC TTC CCG CTA GGC ATT GTT CCG CTG CTG CTG C-3'(Z302, SEQ ID NO: 22) and 5'AGT CGA CTT TGC CAA GGC GTT T-3'(Z337, SEQ ID NO: 23) for *M. tuberculosis;* 5'-ACG ACA GCC TGG GCG ATC GGC T-3'(Z369, SEQ ID NO: 21 ) for *M. fortuitum;* 5'-TCT GGG CGC CCG GTT GCT CAC CTT T-3'(Z366, SEQ ID NO: 15) for *M. gordonae;* 5'-TCC GCG ATC GTC GGG CAT GAG AAG GCC CTC GCG TTC A-3'(Z309, SEQ ID NO: 18) for *M. xenopi;* 5'-TGA CAC ACT CGG CAG CAG GCT GCT CAC CTT CCA GCT T-3'(Z306, SEQ ID NO: 20) for *M. scrofulaceum;* 5'-GTC CCC GAA CGG CGG AGA CAA GCC GAC CGG AGA TCT C-3'(Z304, SEQ ID NO: 16) for *M. simiae;* 5'-CCA GAC GAA CTT TCC ACT CGG A-3'(Z340, SEQ ID NO: 19) for *M. kansasii;* and 5'-GTC CTT CGA CAA GTT CCG AGC GCA ATT CAG CGC CGC C-3'(Z301, SEQ ID NO: 14) for *M. avium/M. brunense.*

Other regions within the sequences of the amplicons obtainable with the primers Z205 and Z212 may also be used to design species specific probes.

The methods provided by the present invention for the diagnosis of infections caused by pathogenic organisms comprise the steps of amplifying the target sequence if present and detecting and identifying the amplicon, if any, by means of probe hybridization assays.

An important aspect of the present invention is the amplification of a part of a gene coding for a SOD. Those practicing the present invention should note that, although the polymerase chain reaction is the preferred amplification method, amplification of target sequences in a sample may be accomplished by any known method, such as a ligase chain reaction (LCR), transcription amplification and self-sustained sequence replication and other methods not listed here, each of which provides sufficient amplification so that the target sequence can be detected by nucleic acid hybridization to one or more appropriate probes.

Although the PCR process is well known in the art (see U.S. Pat. Nos. 4,683,195; 4,683,202 and 4,965,188), some general PCR information is provided below for purposes of clarity and full understanding of the invention to those unfamiliar with the PCR process.

To amplify a target nucleic acid sequence in a sample by PCR, the sequence must be accessible to the components of the amplification system. In general, this accessibility is ensured by isolating the nucleic acids from the sample. A variety of techniques for extracting nucleic acids from biological samples are known in the art. For example, see those described in Higuchi et al., PCR Technology (Erlich ed., Stockton Press, New York, 1989). Alternatively, if the sample is fairly readily disruptable, the nucleic acid need not be purified prior to amplification by the PCR technique, i.e., if the sample is comprised of cells, particularly peripheral blood lymphocytes or aminiocytes, lysis and dispersion of the intracellular components can be accomplished merely by suspending the cells in hypotonic buffer.

Each cycle of the PCR involves the separation of the nucleic acid duplex formed by primer extension. In a preferred embodiment of the PCR process, strand separation is achieved by heating the reaction to a sufficiently high temperature and for an effective time to cause the denaturation of the duplex, but not to cause an irreversible denaturation of the polymerase (see U.S. Pat. No. 4,965,188). Typical heat denaturation involves temperatures ranging from about 80° C. to 105° C. for times ranging from seconds to minutes. Strand separation, however, can be accomplished by any suitable denaturing method including physical, chemical or enzymatic means. Strand separation can be induced by a helicase, for example, or an enzyme capable of exhibiting helicase activity. For example, the enzyme RecA has helicase activity in the presence of ATP. The reaction conditions suitable for strand separation by helicases are known in the art; cf. Kuhn Hoffman-Berling, CSH-Quantitative Biology 43, 63–67 (1978) and Radding, Ann. Rev. Genetics 16, 405–436 (1982).

No matter how strand separation is achieved, however, once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

Template-dependent extension of primers in PCR is catalyzed by a polymerizing agent in the presence of adequate amounts of deoxyribonucleoside triphosphates (usually dATP, dGTP, dCTP and dTTP; dUTP is used in place of or in addition to dTTP if the UNG sterilization system described below is incorporated) in a reaction medium comprised of the appropriate salts, metal cations, and pH buffering system. Suitable polymerizing agents are enzymes known to catalyze template-dependent DNA synthesis. Examples of polymerases suitable for use with a DNA template include *E. coli* DNA polymerase I or the Klenow fragment of that enzyme, $T_4$ DNA polymerase and Taq DNA polymerase, a heat stable DNA polymerase isolated from Thermus aquaticus. The latter enzyme is widely used in the amplification and sequencing of nucleic acids. The reaction conditions for using Taq DNA polymerases are known in the art and are described in Gelfand, PCR Technology (1989), supra. Other heat stable polymerases may also be suitable.

The PCR method can be performed in a stepwise fashion, where after each step new reagents are added, or in a fashion where all of the reagents are added simultaneously, or in a partial stepwise fashion, where fresh or different reagents are added after a given number of steps. For example, if strand separation is induced by heat and the polymerase is heat sensitive, then the polymerase has to be added after every round of strand separation. However, if, for example, a helicase is used for denaturation, or if a thermostable polymerase is used for extension, then all of the reagents may be added initially, or, alternatively, if molar ratios of reagents are of consequence to the reaction, the reagents may be replenished periodically as they are depleted by the synthetic reaction.

Those skilled in the art will know that the PCR process is most usually carried out as an automated process with a thermostable enzyme. In this process, the temperature of the reaction mixture is cycled through a denaturing region, a primer annealing region and a reaction region. A machine (thermocycler) specifically adapted for use with a thermostable enzyme is commercially available.

Those skilled in the art will also be aware of the problem of contamination of a PCR by the amplified nucleic acid from previous reactions. Methods to reduce this problem allow for the enzymatic degradation of any amplified DNA from previous reactions. The PCR amplification is carried out in the presence of dUTP instead of dTTP. The resulting double stranded uracil containing product is subject to degradation by uracil N-glycosylase (UNG), whereas normal thymine-containing DNA is not degraded by UNG. Adding UNG to the amplification reaction mixture before the amplification is started degrades all uracil containing DNA that might serve as target. Because the only source of uracil containing DNA is the amplified product of a previous reaction, this method effectively sterilizes the reaction mixture, eliminating the problem of contamination from previous reactions (carryover). UNG is rendered temporarily inactive by heat, so the denaturation steps in the amplification procedure also serve to inactivate the UNG. New amplification products, therefore, though incorporating uracil, are formed in an UNG-free environment and are not degraded.

Another important aspect of the present invention is probe hybridization. The oligonucleotide probes of the present invention hybridize specifically with a particular segment of the SOD gene of an organism to be detected and identified and have sufficient destabilizing mismatches with the sequences from different organisms in the case of genus specific probes, and other species of the same genus in the case of species specific probes.

The probes of the invention can be used to determine if nucleic acid sequences are present in a sample by determining if the probes bind to the sequences present in the sample. Suitable assay methods for purposes of the present invention to detect hybrids formed between probes and nucleic acid sequences in a sample are known in the art. For example, the detection can be accomplished by Southern blotting and liquid hybridization using a dot blot format. In the dot blot format, the unlabeled amplified sample is bound to a solid support, such as a membrane, the membrane incubated with labeled probe under suitable hybridization conditions, the unhybridized probe removed by washing, and the filter monitored for the presence of bound probe. When multiple samples are analyzed with few probes, such as is the case when samples are screened for the presence of nucleic acid of a particular genus using genus specific probes, the dot blot format is quite useful.

An alternate method is quite useful when large numbers of different probes are to be used. This method is a "reverse" dot blot, in which the amplified sequence contains a label, and the probe is bound to the solid support. In this format, the unlabeled probes are bound to the membrane and exposed to the labeled sample under appropriate hybridization conditions. Unhybridized labeled sample is then removed by washing under suitable conditions, and the filter is then monitored for the presence of bound sequences. Because species determination requires the use of multiple species specific probes for each amplified sample, the reverse dot blot format is the preferred test format for this step.

Alternatively, it may be desirable to use a detection method having a plurality of probe hybridization sites or wells. For example, a solid support such as a microtiter plate is particularly useful in large scale clinical applications of the present methods. Methods for hybridization/capture of PCR amplified DNA or solid supports are known. In one embodiment of those methods the amplified target DNA is labeled (e.g., with biotin) during amplification in the PCR reaction. The labeled DNA is specifically captured by hybridization of PCR product to a target-specific oligonucleotide capture probe that has been bound to the microtiter plate well. The bound product is suitably detected according to the type of label used. For example, if biotin is used as a label, avidin HRP complex is added and is reacted with either (a) hydrogen peroxide substrate and O-phenylene diamine (OPD) chromogen or (b) hydrogen peroxide substrate and tetramethylbenzidine chromogen (TMB). A color metric signal develops, allowing for the quantitative detection of the PCR amplified DNA.

As practiced in laboratories, detection procedures using microtiter plate assays can be standardized for a wide range of targets. It may be necessary to individually determine the appropriate hybridization and stringency conditions to insure the maximum specificity taking into account the length of the probes utilized.

In another suitable assay system a labeled probe is added during the PCR amplification process. Any probe that hybridizes to target DNA during each synthesis step is degraded by the 5' to 3' exonuclease activity of the polymerase used to catalyze primer extension. The degradation product from the probe is then detected. Thus, the presence of the degradation product indicates that the hybridization between the probe and the target DNA occurred.

The present invention also relates to sets of reagents for amplifying a part of a gene coding for a superoxide dismutase (SOD), especially an SOD of a mycobacterial species, as well as to sets of reagents for detecting a mycobacterial species and for differentiating among different species belonging to the genus of mycobacteria.

The sets of reagents for the amplification comprise the primers according to the present invention, i.e a pair of universal primers and/or a pair of primers suitable for the amplification of a part of the SOD genes of the different species belonging to a particular genus, especially a pair of primers suitable for the amplification of a part of the SOD genes of mycobacterial species. They may optionally also contain a DNA polymerase, e.g. one of the aforementioned DNA polymerases, and/or the substrate nucleoside triphosphates mentioned above and/or the appropriate buffers for PCR. In addition to the above components, the sets of reagents may also contain instructions for carrying out the amplification according to the present invention.

The sets of reagents for detecting a mycobacterial species comprise one or more genus specific probes, especially a pool of genus specific probes according to the present invention. In some cases, the probes may be fixed to an appropriate support membrane. Other optional components of the kit include, for example, means used to label and/or detect label (for example, an avidin-enzyme conjugate and enzyme substrate and chromogen if the label is biotin), and the appropriate buffers for hybridization reactions. In addition to the above components, the sets of reagents may also contain instructions for carrying out the detection methods according to the present invention.

The sets of reagents for differentiating among different species belonging to the genus of mycobacteria comprise one or more species specific probes according to the present invention. In some cases, the probes may be fixed to an appropriate support membrane. Other optional components of the kit include, for example, means used to label and/or detect label (for example, an avidin-enzyme conjugate and enzyme substrate and chromogen if the label is biotin), and the appropriate buffers for hybridization reactions. In addition to the above components, the sets of reagents may also contain instructions for carrying out the differentiation methods according to the present invention.

The sets of reagents for detecting a mycobacterial species and for differentiating among different species belonging to the genus of mycobacteria may additionally also contain one or more of the components mentioned above for the sets of reagents for the amplification.

In another embodiment of the present invention, the sets of reagents for the amplification, detection and differentiation may also contain positive and/or negative controls. Preferably a positive control includes a nucleic acid sequence that is amplifiable using the same primer pair used to amplify the desired target nucleic acids in a test sample. Methods for using a positive control, wherein both the target that may or may not be present and the positive control use the same primer pair, are known to those skilled in the art. Preferably the positive control is designed so that the product DNA is of a discrete size readily distinguishable from the size of the target or is modified in ways known to those skilled in the art (mutations/restriction sites).

The following examples are intended to describe the present invention in more detail. They are only for illustrative purposes and not to limit the scope of the invention in any way.

BRIEF DESCRIPTION OF THE TABLES

Table 1a: Provides data showing the mycobacterial species, their origin, amplification with the universal primers Z205 and Z212, amplification with the genus specific primers Z261 and Z212 and hybridization with the genus specific pool of probes Z310–Z317.

Table 1b: Provides data showing the mycobacterial species, their origin Z304 (*M. simiae*); Z340 (*M. kansasii*); Z306 (*M. scrofulaceum*); Z366 (*M. gordonae*); Z369 (*M. fortuitum*); and Z309 (*M. xenopi*).

Table 2a: Provides data showing the non-mycobacterial species, their origin, amplification with the universal primers Z205 and Z212, amplification with the genus-specific primers Z261 and Z212 and hybridization with the genus specific pool of probes (Z310–Z317).

Table 2b: Provides data showing the non-mycobacterial species, their origin and hybridization with the species-specific probes mentioned above for Table 1b.

Table 3: Shows the sequence of primers used in the sequencing of the amplicons obtained with primers Z205 and Z212 after cloning in pUC 19.

Table 4: Shows the DNA-sequence of the amplicons obtained with primers Z205 and Z212 being part of the SOD-gene of *M. tuberculosis*.

Table 5: Shows the DNA-sequence of the amplicons obtained with primers Z205 and Z212 being part of the SOD-gene of *M. avium*.

Table 6: Shows the DNA-sequence of the amplicons obtained with primers Z205 and Z212 being part of the SOD-gene of *M. intracellulare*.

Table 7: Shows the DNA-sequence of the amplicons obtained with primers Z205 and Z212 being part of the SOD-gene of *M. scrofulaceum*.

Table 8: Shows the DNA-sequence of the amplicons obtained with primers Z205 and Z212 being part of the SOD-gene of *M. kansasii*.

Table 9: Shows the DNA-sequence of the amplicons obtained with primers Z205 and Z212 being part of the SOD-gene of *M. fortuitum*.

Table 10: Shows the DNA-sequence of the amplicons obtained with primers Z205 and Z212 being part of the SOD-gene of *M. simiae*.

Table 11: Shows the DNA-sequence of the amplicons obtained with primers Z205 and Z212 being part of the SOD-gene of *M. gordonae*.

Table 12: Shows the DNA-sequence of the amplicons obtained with primers Z205 and Z212 being part of the SOD-gene of *M. xenopi*.

Table 13: Shows the DNA-sequence of the amplicons obtained with primers Z205 and Z212 being part of the SOD-gene of Corynebacterium diphteriae.

Table 14: Shows the DNA-sequence of the amplicons obtained with primers Z205 and Z212 being part of the SOD-gene of Corynebacterium pseudodiphtheriticum.

Table 15: Shows the DNA-sequence of the amplicons obtained with primers Z205 and Z212 being part of the SOD-gene of Nocardia asteroides.

Table 16: Shows the DNA-sequence of the amplicons obtained with primers Z205 and Z212 being part of the SOD-gene of Actinomyces viscosus.

Table 17: Shows the sequence of the consensus-primer Z261 and the mismatches within the 9 sequenced species of the genus mycobacteria, the 4 sequenced non-mycobacterial organisms as well as the corresponding part sequence derived from *E. coli*- and the human SOD-gene.

Table 18: Provides the consensus sequence of the genus-specific probe for mycobacteria, the mismatches within the 4 sequenced non-mycobacterial organisms as well as the corresponding part of the sequence derived from *E. coli*- and the human SOD-gene. The sequence of the individual oligonucleotides the genus-specific pool is composed of are also listed.

EXAMPLE 1

Amplification of Mycobacterial SOD-Sequences with the Primers Z205 and Z212

The primers were synthesized on a MilliGen/Biosearch Cyclone Plus Synthesizer using the DNA synthesizing kit for sequences of up to 50 nucleotides (Millipore GmbH, Eschborn FRG). The oligonucleotides were eluted from the cartidges with 25% $NH_4OH$, dried in vacuo, and dissolved without further purification to a final concentration of 20 µM.

About 1 ng of previously purified chromosomal DNA of the mycobacterial species listed in Table 1 a and the non-mycobacterial species listed in Table 2a, were amplified by a PCR with the following cycling profile in a Thermocycler 480 (Perkin Elmer): Heat for 5 min at 98° C. (initial denaturation), cool to 55° C. before the addition of 5 U of Taq polymerase (Perkin Elmer AG, Küsnacht, Switzerland), and cycle 35 times for 30 sec at 94° C. (denaturation), 30 sec at 37°–55° C. (annealing), 30 sec at 72° C. (extension) and hold for 10 min at 72° C.

A standard PCR reaction consisted of: 10 µl 10 ×buffer (100 mM of Tris; pH=8.3 at room temperature; 500 mM of KCl; 15 mM of $MgCl_2$; 0.015% of gelatine), 16 µl of deoxyribonucleotide-mix (1.25 µmol of each dATP; dGTP; dCTP; dTTP), 5 µl of primer Z205 (20 µM), 5 µl of primer Z212 (20 µM), 10 µl of DNA to be amplified and 53 µl of $H_2O$. 10 µl of the amplified mixtures were loaded on 1% agarose gels and separated at 200 V, using the 123 bp and the 1 kb ladder as size standards (Bethesda Research Laboratories, Gaithersburg). After appropriate separation, the gels were stained with ethidiumbromide and photographed. For further experimental details see: Molecular Cloning, 1989, J. Sambrook, E. F. Fritsch, T. Maniatis; (eds.); Cold Spring Harbor Laboratory Press.

The results are compiled in Tables 1 a and 2a; a "+" indicates that a visible amplicon was obtained. Using the primer pair Z205 and Z212 at an annealing temperature of 37° C., all DNA preparations from the 27 different species of Mycobacteria tested (listed in Table 1a) and all the 106 non-mycobacterial species listed in Table 2a gave visible amplicons on stained gels. The most predominant (and in most cases the only visible fragment) was a DNA fragment co-migrating with the predicted amplicon from *M. tuberculosis* of 489 bp spanning the region 188 to 678 of the *M. tuberculosis* sequence. Therefore, the primer pair Z205 and Z212 can be viewed as universal primers.

EXAMPLE 2

Cloning and Sequencing the Amplicons from selected bacteria obtained with primers Z205 and Z212

The region corresponding to positions 188 to 666 within the SOD gene of *M. tuberculosis* of the 9 mycobacterial species and the 4 non-mycobacterial species listed below was amplified using the primer pair Z205 and Z212. The amplicons were subsequently cloned and sequenced as described hereinafter:

*M. tuberculosis* (ATCC 1400); *M. avium* (ATCC 25291); *M. intracellulare* (DSM 43223); *M. scrofulaceum* (ATCC 19981); *M. kansasii* (DSM 43224); *M fortuitum (ATCC* 6841); *M. simiae* (ATCC 25275); *M. gordonae* (DSM 610); *M. xenopi* (ATCC 19250); *Corynebacterium diphteriae* (ATCC 11913); *Corynebacterium pseudodiphteriticum* (RC 181); *Nocardia asteroides* (ATCC 43005); and *Actinomyces viscosus* (ATCC 15987).

Details of the procedures can be found in the previously referenced laboratory manual: "Molecular Cloning". About 1 ng of chromosomal DNA from the 13 organisms listed above were amplified as described in Example 1. The possibly frayed ends of the PCR amplicons were filled-in using the four deoxynucleotides (dNTP) and Klenow polymerase. Unincorporated primers and dNTP's were separated from the amplicons by diluting the reaction and passing the solution over a Quiagen tip 5 following the instructions of the manufacturer (Diagen, Düsseldorf, FRG). The eluted and precipitated DNA was dissolved and phosphorylated using a 5'-endlabeling-kit (Boehringer Mannheim GmbH, Mannheim, FRG). The filled-in and kinased amplicons were separated by electrophoresis on NuSieve GTG agarose (FMC, BioProducts Europe, Vallensbaek Strand, Denmark) and the amplicons co-migrating with the 489 bp fragment of *M. tuberculosis* were excised. The DNA was recovered from the gel slices and purified with a Quiagen tip 5 as described above. The pellet obtained after precipitation was dissolved, quantitated and used for ligation.

The plasmid pUC 19 was digested to completion with SmaI, phenol extracted, precipitated and dissolved before being dephosphorylated with calf thymus alkaline phosphatase. The vector DNA was again phenol extracted, precipitated and diluted to about 1 ng/μl. Vector DNA and all enzymes used in the vector preparation were from Boehringer Mannheim (Mannheim, FRG).

The digested, dephosphorylated vector DNA was ligated to the purified SOD amplicons for 18 h at 22° C. using 1 U T4-ligase. DH5a competent cells (Bethesda Research Laboratories, Gaithersburg, U.S.A.) were transformed with 2–5 gl of the ligase mixture, following the instructions of the supplier and plated on LB-agar with X-gal, IPTG and ampicillin (for details see "Molecular Cloning").

From each transformation of the 13 cloned amplicons, ten recombinant (colorless) colonies were picked and grown in 200 μl of LB-broth dispensed into a well of a microliter plate. A crude DNA preparation was formed using a boiling-freezing method and appropriate aliquots of the DNA solution were amplified without further purification by a PCR using the pUC-sequencing and reverse sequencing primers (Boehringer Mannheim; Mannheim, FRG). Two wells from each of the 13 different amplifications containing plasmids with the expected insert size of 592 bp (103 bp stemming from the multiple cloning site and 489 bp from the SOD amplicon) were used for further sequencing. The recombinant plasmid DNA from 2 independent clones from each of the 13 different organisms listed above was purified using the Quiagen "Plasmid" maxi kit (Diagen, Düsseldorf, FRG) and sequenced by the dideoxymethod using the pUC sequencing kit with $S^{35}$ following the instructions given by the manufacturer (Boehringer Mannheim, Mannheim, FRG).

The position of the primers used for sequencing is shown in FIG. 1. Besides the two primers annealing in the multiple-cloning site of pUC 19 (pUC forward and pUC reverse), the same two primers used for cloning (Z205 and Z212) were used in the sequencing reactions. For all mycobacterial species and Nocardia asteroides, two additional forward primers (Z256 and Z243) and one reverse primer (Z244) were used. This strategy allowed perfect overlapping reading of the sequencing-gels with only about 150 bp to be read from any one reaction. The positions of the primers specific for the sequencing of the SOD-amplicons from the remaining commensalic bacteria (Z257 and Z245 for *C. diphteriae*, Z258 and Z247 for *C. pseudodiphteriticum* and Z246 for *A. viscosus*) are also indicated in FIG. 1. The sequence of all sequencing primers within the SOD gene is given in Table 3. Since primer Z212 contains 2 wobble bases, it was possible to ensure that two independent clones were sequenced from each of the 13 species.

A total of 29.1 kb were read from the 26 clones derived from 9 mycobacterial and 4 non-mycobacterial species, The consensus sequences are shown in Tables 4–16.

EXAMPLE 3

Comparison of SOD Sequences to determine Mycobacteria Specific PCR Primers

Each of the SOD sequences shown in Tables 4–16 were aligned to allow comparison to each other in order to identify the regions of pronounced homology within the members of the genus mycobacteria and pronounced heterogeneity when compared to the corresponding regions from the non-mycobacterial species. The GCG-program (Genetics Computer Group Sequence Analysis software, Version 7.1, Dervereux et al., NAR 12, 387–395 (1984); GAP-Alignment) was used for alignment.

In this way, primers specific for all the 27 species of the genus mycobacteria could be derived which would allow the amplification of the part of their SOD-coding sequences flanked by the primers annealing to the conserved regions. These conserved regions within the genus mycobacteria exhibit a number of mismatches when compared to the corresponding regions of the 4 sequenced non-mycobacterial species. Therefore, primers selected by those criteria most likely would prevent the amplification of non-mycobacterial species.

The primer sequences selected (Z261 and Z212) were one of several combinations tested for their ability to amplify all 27 species of mycobacteria (Table 1a), but none of the 93 non-mycobacterial target DNA's (Table 2a). One of the two primers (Z212) was used to amplify both the mycobacterial and the non-mycobacterial DNA's. The sequence of Z212 corresponds to positions 677–655 within the SOD-gene of *M. tuberculosis.* The discriminatory amplification of the DNA from mycobacterial and non-mycobacterial species therefore rests with the counterprimer Z261 (positions 245–269 within the SOD gene of *M. tuberculosis*). The sequence of Z261 together with the mismatches within the 9 sequenced species of the genus mycobacteria and the 4 selected non-mycobacterial species is shown in Table 17. With the introduction of two wobble bases (positions 249 and 264), a maximum of 2 mismatches remain with the 9 sequenced mycobacterial species. The last 5 nucleotides at the 3'-end of the primer are conserved among all the 9 sequenced mycobacteria.

EXAMPLE 4

Amplification with Genus Specific Primers Z261 and Z212

Using DNA from *M. tuberculosis*, the amplicons obtained with the primer pair Z261/Z212 were 434 bp long. The annealing temperature for the genus specific amplification was optimized using DNA from *M. tuberculosis, M. intracellulare, C. diphteriae, Nocardia asteroides* and human DNA as representative test DNA's using the PCR standard conditions described in Example 1. The following temperatures were evaluated: 37° C.; 45° C.; 50° C.; 55° C.; 58° C.; 60° C.; 64° C.; 67° C. and 70° C.; the amplicons seen with non-mycobacterial DNA at non-stringent temperatures (37° C. and 45° C.) started to disappear at higher annealing temperatures (>58° C.). At 64° C. a series of fragments could still be seen with human DNA which were not present at 67° C. Either 60° or 67° C. was used with the primer pair Z261 and Z212. The visible amount of amplicons was higher with 60° C. although 67° C. was clearly the more discriminatory temperature. The optimal magnesium concentration was found to be 1.5 mM. Therefore, the final cycling protocol for the genus specific primers (Z261 and Z212) was as follows: Heat for 5 min at 98° C., cool to 55° C., add 1 µl of Taq (5 U) and amplify for 35 cycles, 30 sec each, 94° C., 60° or 67° C., 72° C. followed by a 10 min incubation at 72° C.

The results are compiled in Tables 1 a and 2a; a "+" indicates that visible amplicons were obtained and a "−" indicates that no or very few amplicons were obtained. All 27 mycobacterial species were amplified with the genus specific primers Z261 and Z212, as verified by gel electrophoresis, using an annealing temperature of 67° C. (Table 1a). However the signals obtained on gels with *M. gadium, M. marinum* and *M. haemophilum* were weak compared to the signals of the other 24 species. After increasing the cycling time to 1 min, visible signals were obtained also with the 3 species in question.

The primers Z261 and Z212 did not amplify 102 out of the 106 non-mycobacterial species (Table 2a) as judged by the absence of visible signals on agarose gels. To ensure that the correct amount of amplifiable material was introduced in the PCR-reaction, all DNA's were tested (and found positive) in parallel with the primer pair Z205 and Z212. Four bacterial species gave weak signals on gels with the PCR-conditions used, namely: *Edwardsiella tarda, Ewingella americana, Klebsiella pneumoniae* and *Salmonella hautena*. However, none of the amplicons from these 4 species corresponded exactly in size and intensity to the amplicons obtained with the mycobacterial DNA.

EXAMPLE 5

Selection of Genus Specific Probes

The sequences obtained by amplifying the 9 mycobacterial and 4 non-mycobacterial DNA's with the genus specific primers Z261 and Z212 (Tables 4–16) were aligned and analyzed for regions of maximum homology within the mycobacteria and maximum heterogeneity among the non-mycobacterial species. The genus specific probe finally selected covers position 382 to 421 in the *M. tuberculosis* sequence. The common sequence is shown in Table 18, together with the mismatches present in the sequenced non-mycobacterial species. Only 2 mismatches occur in Nocardia asteroides, but this DNA does not amplify under the conditions described with the genus specific PCR primer Z261 and Z212, due to 11 mismatches present. Instead of introducing a total of 14 wobble bases to cover all mismatches within the 9 sequenced species of mycobacteria (Table 18), we opted to synthesize each of the genus-specific oligos separately, resulting in a pool of 8 oligonucleotides (*M. intracellulare* and *M. xenopi* are grouped together) where each of the individual probes is present in equimolar amounts. The sequence of the oligos constituting the genus specific pool of probes is shown in Table 18. Probe Z310 detects *M. tuberculosis*, Z311 both *M. intracellulare* and *M. xenopi*, Z312 *M. avium*, Z313 *M. gordonae*, Z314 *M. fortuitum*, Z315 *M. scrofulaceum*, Z316 *M. simiae* and Z317 *M. kansasii*.

EXAMPLE 6

Hybridization with Genus Specific Probes

The genus specific pool of probes (Table 18) was labeled as follows: (80 pmol of an equimolar mix of the 8 probes (Z310–Z317) were labeled at the 5'-end to a specific activity of about $3 \times 10^7$/µg using 100 γCi of $^{32}$P-γ ATP (10 mCi/ml; 5000 Ci/mmol) following the instructions given by the supplier of the 5'-labeling kit (Boehringer Mannheim, Mannheim, FRG). The unincorporated label was removed using a Biospin 6 column (BioRad, Richmond, U.S.A.). 20 µl of alkali-denatured PCR mixtures obtained with the genus specific primers Z261 and Z212 from the 27 mycobacterial species (Table 1a) and 106 non-mycobacterial species (Table 2a) were diluted with 100 µl TE-buffer and spotted on prewetted solid supports ("Gene Screen plus" filters; Du Pont de Nemours, Bad Homburg, FRG) using a 96-well manifold (Schleicher & Schuell, Dassel, FRG). The filters were crosslinked in a Stratagene UV-linker (Statagene, La Jolla, U.S.A.) and prehybridized in a 50 ml Falcon tube containing 5 ml of prehybridization solution (6× SSC, 10 mM sodium phosphate pH 6.8, 1 mM EDTA pH 8.0, 1% SDS, denatured salmon sperm DNA 100 µg/ml). Prehybridization was performed at 60° C. for 60 min in a rotating hybridization oven. The prehybridization fluid was discarded and replaced by 5 ml of hybridization solution (3M tetramethylammonium chloride, 10 mM sodium phosphate pH 6.8, 1 mM EDTA pH 7.6, 0.5% SDS, denatured salmon sperm DNA 100 µg/ml and $5-8 \times 10^6$ cpm of labeled genus specific probes. Details of the buffer preparation can be found in the "Molecular Cloning" compendium referred to earlier. Hybridization was performed for 3–16 h at 65° C. The filters were washed for 4×15 min in prewarmed (70° C.) 2 X SSC/0.2% SDS at 70° C. before being autoradiographed for 1–2 h at −70° C. using intensifying screens.

The results are compiled in Tables 1a and 2a; a "+" indicates that a hybridization signal was obtained and a "−" indicates that no hybridization signal was obtained. The genus specific pool of probes (Z310–Z317) was used to probe all 27 species of mycobacteria (Table 1a). The pool recognized all 9 sequenced species of mycobacteria (Tables 4–12), specifically: *M. tuberculosis, M. avium, M. intracellulare, M. fortuitum, M. scofulaceum, M. gordonae, M. simiae, M. xenopi* and *M. kansasii*. In addition, the following 13 non-sequenced species of mycobacteria are recognized with the genus specific probe pool: *M. africanum, M. acapulcensis, M. bovis, M. brunense, M. chelonai, M. flavescens, M. marinum, M. gastri, M. terrae, M. triviale, M. nonchromaticum, M. oboense* and *M. smegmatis* (indicated by "+" in Table 1a). Weaker signals under the hybridization conditions described were obtained with: *M. haemophilum, M. gadium, M. szlugai* and *M. plei* (indicated by "(+)" in Table 1a). No signal was obtained with *M. rhodensiae* (indicated by "(−)" in Table 1a).

None of the amplicons obtained with the genus-specific primers Z261 and Z212 from the non-mycobacterial species listed in Table 2a (not being visible on gels) as well as the 4 species which gave weak visible signals on gels; see Example 7) was detected with the pool of genus specific probes (Z310–Z317). The results are summarized in Table 2a.

EXAMPLE 7

Identification of Species Specific Probes

The sequences of the amplicons obtained by amplifying the 9 mycobacterial DNA's with the genus specific primers Z261 and Z212 (Tables 4–12) were aligned as described in Example 3 and each of the mycobacterial sequences were analyzed one by one for regions of pronounced heterogeneity when compared to the remaining mycobacterial sequences. In this way, species specific sequences could be identified and experimentally analyzed. The regions which numerically showed the highest number of mismatches (maximal heterogeneity in the alignment program used) turned out to be not always the regions which resulted in the most discriminatory hybridization results. Noteworthy is also that the number of mismatches of one sequence when compared to the others depends on the criteria used for the alignments. The positions given for the species specific probes refer to the sequences they are derived from (Tables 4–12), and not to the numbers attributed to them in the different alignment programs.

EXAMPLE 7.1

*M. tuberculosis* Specific Probe

Three regions were selected with the following sequences (Table 4): Z302: 5'-ACG AAC TTC CCG CTA GGC ATT GTT CCG CTG CTG CTG C-3' (SEQ ID NO: 22; position 550–586); Z336: 5'-GCT AGG CAT TGT TCC GCT GCT GCT GC-3' (SEQ ID NO: 17; position 561–586); and Z337: 5'-AGT CGA CTT TGC CAA GGC GTT T-3' (SEQ ID NO: 23; position 633–654).

Z302, Z336 and Z337 were labeled and hybridized as described in Example 6 against filters on which 28 mycobacterial amplicons (26 different species) obtained with Z261 and Z212 were immobilized. The hybridization temperature was 70° C. for Z302 and 60° C. for the remaining two probes. The hybridization was carried out for 1–16h, the washing temperature was 80° C. for Z302, 65° C. for Z337 and 60° C. for Z336. The films were exposed for 1–3 h.

The probe Z302, being 37 nucleotides long, recognized under the conditions used only *M. tuberculosis* and the close relatives combined in a "macrocluster" (Bergey's Manual of Determinative Bacteriology, 1974, 8<sup>th</sup> Edition, Waverly Press Inc, Baltimore, R. E. Buchanon+N. E. Gibbons (Eds.)) with *M. bovis, M. bovis BCG* and *M. africanum*. The remaining 23 mycobacterial species listed in Table 1b were not recognized by Z302 nor any of the 106 non-mycobacterial species listed in Table 2b.

Probe Z336 represents the last 26 nucleotides on the 3'-end of the original probe Z302. The truncated probe Z336 hybridized under the modified conditions described only to *M. tuberculosis, M. bovis, M. boris BCG* and *M. africanum*. No crossreaction is seen with the remaining 23 mycobacterial species listed in Table 1b, nor with any of the 106 non-mycobacterial species listed in Table 2b.

Z337 (a probe of 22 nucleotides) positioned towards the end of the sequenced part of the SOD gene is specific for the *M. tuberculosis-M. bovis-M. africanum* complex and does not cross react with the remaining 23 mycobacterial species listed in Table 1b, nor with any of the 106 non-mycobacterial species listed in Table 2b.

Although the specificity of the three probes Z302, Z336 and Z337 is comparable, the probes Z336 and Z337 are preferred ones due to the lower washing temperature.

EXAMPLE 7.2

*M. avium-M. brunense* Specific Probe

The region 423–459 (Table 5) was selected with the following sequence: Z301:5'-GTC CTT CGA CAA GTT CCG AGC GCA ATT CAG CGC CGC C-3' (SEQ ID NO: 14; position 423–459). Z301 was labeled and hybridized as described in Example 6 against a filter on which mycobacterial amplicons obtained with Z261 and Z212 were immobilized. Hybridization was performed for 1–16 h at a temperature of 70° C. for Z301, the washing temperature was 80° C. for Z301. The films were exposed for 3 h. With the *M. avium-M. brunense* specific probe Z301, the amplicons from *M. avium* were recognized together with the amplicons from *M. brunense* (n=6; amplicons derived from the same stock DNA preparation). There are no sequencing data available for *M. brunense* and thus no rational probe design was possible for this species. It can not be entirely ruled out at this point that the stock of *M. brunense* was in fact contaminated with *M. avium* amplicons. Until new stocks of *M. brunense* are grown, amplified and sequenced Z301 is described as a probe recognizing both *M. avium* and *M. brunense*. Z301 did not recognize any of the other mycobacterial species listed in Table 1b. Again none of the tested non-mycobacterial DNA's listed in Table 2b cross-reacted with the *M. avium-M. brunense* specific probe.

EXAMPLE 7.3

*M. intracellare* Specific Probe

The region 416–452 (Table 6) was selected with the following sequence: Z303:5'-CCT TCG GAT CCT TCG ACC GGT TCC GCG CGC AGT TCA G-3' (SEQ ID NO: 13).

Figure 2:
FIG. 2 shows a dot blot with immobilized amplicons obtained with the genus-specific primers Z261 and Z212 hybridized against the probe Z303, specific for *M.intracellulare*.

Z303 was end-labeled and hybridized as described in Example 6 against a filter on which 28 mycobacterial amplicons (26 different species) obtained with Z261 and Z212 were immobilized. The hybridization was performed at 60° C. for 16 h, the washing temperature was 70° C. and the films were exposed for 3 h, 6 h and 16 h. An example of the specificity of the species specific probe selected for *M. intracellulare* is shown in FIG. 2 (16 h exposure) and the results are summarized in Table 1b.

The arrangements of DNA on the filter was as follows:

| | | |
|---|---|---|
| A 2 | *M. tuberculosis* (clinical isolate 1400) | |
| A 3 | *M. tuberculosis* | 27294 |
| A 4 | *M. avium* | 25291 |
| A 5 | *M. fortuitum* | 6841 |
| A 6 | *M. gordonae* | DSM 610 |
| A 7 | *M. kansasii* | DSM 43224 |
| A 8 | *M. scrofulaceum* | 19981 |
| A 9 | *M. simiae* | 25275 |
| A 10 | *M. xenopi* | 19250 |
| A 11 | *M. intracellulare* | DSM 43223 |
| B 2 | *M. acapulcensis* | 14473 |
| B 3 | *M. africanum* | 25420 |
| B 4 | *M. bovis BCG* | 1401 |
| B 5 | *M. bovis* | 19210 |
| B 6 | *M. brunense* | 23434 |
| B 7 | *M. chelonai* | 35752 |
| B 8 | *M. flavescens* | DSM 43219 |
| B 9 | *M. gastri* | 15754 |
| B 10 | *M. smegmatis* | 14468 |
| B 11 | *M. terrae* | 15755 |
| C 2 | *M. triviale* | 23292 |
| C 3 | *M. marinum* | 927 |
| C 4 | *M. haemophilum* | 29548 |
| C 5 | *M. nonchromogenicum* | 19530 |

| C 6 | M. obuense | 27023 |
| C 7 | M. phlei | DSM 750 |
| C 8 | M. rhodesiae | 27024 |
| C 9 | M. szulgai | 35799 |
| C 10 | M. gadium | 27726 |
| | H₂O | |

None of the 106 tested species of non-mycobaterial organisms did react under the same conditions as described above for the mycobacterial species.

EXAMPLE 7.4 M. scrofulaceum Specific Probe

The region 501–537 (Table 7) was selected with the following sequence: Z306:5—TGA CAC ACT CGG CAG CAG GCT GCT CAC CTT CCA GCT T-3' (SEQ ID NO: 20).

Z306 was labeled and hybridized as described in Example 6 against a filter on which 28 mycobacterial amplicons (26 different species) obtained with Z261 and Z212 were immobilized. Hybridization was performed at a temperature of 70° C. for 1–16 h, the washing temperature was 80° C. and the films were exposed for 3 h, 6 h and 16 h. Z306 hybridized only to M. scrofulaceum DNA but not to any of the other mycobacteria listed in Table 1b. None of the 106 tested non-mycobacterial DNA's listed in Table 2b cross-reacted with the M. scrofulaceum specific probe.

EXAMPLE 7.5

M. kansasii Specific probe

The region 546–567 (Table 8) was selected with the following sequence: Z340: 5'-CCA GAC GAA CTT TCC ACT CGG A-3' (SEQ ID NO: 19).

Z340 was labeled and hybridized as described in Example 6 against a filter on which 28 mycobacterial amplicons (26 different species) obtained with Z261 and Z212 were immobilized. Hybridization was performed at a temperature of 60° C. for 1–16 h, the washing temperature was 65° C. and the films were exposed for 3 h, 6 h and 16 h. Z340 hybridized only to M. kansasii DNA but not to any of the other mycobacteria listed in Table 1b. None of the 106 tested non-mycobacterial DNA's listed in Table 2b cross-reacted with the M. kansasii specific probe.

EXAMPLE 7.6

M. fortuitum Specific Probe

The region 500–521 (Table 9) was selected with the following sequence: Z369: 5'-ACG ACA GCC TGG GCG ATC GGC T-3' (SEQ ID NO: 21).

Z369 was end-labeled and hybridized as described in Example 6 against a filter on which 28 mycobacterial amplicons (26 different species) obtained with Z261 and Z212 were immobilized. Hybridization was performed at a temperature of 60° C. for 1–16 h, the washing temperature was 70° C. and the films were exposed for 3 h, 6 h and 16 h. Z369 hybridized only to M. fortuitum DNA but not to any of the other mycobacteria listed in Table 1b. None of the 106 tested non-mycobacterial DNA's listed in Table 2b cross-reacted with the M. fortuitum specific probe.

EXAMPLE 7.7

M. simiae Specific Probe

The region 360–396 (Table 10) was selected with the following sequence: Z304:5'-GTC CCC GAA CGG CGG AGA CAA GCC GAC CGG AGA TCT C-3' (SEQ ID NO: 16).

Z304 was labeled and hybridized as described in Example 6 against a filter on which 28 mycobacterial amplicons (26 different species) obtained with Z261 and Z212 were immobilized. Hybridization was performed at a temperature of 70° C. for 1–16 h, the washing temperature was 80° C. and the films were exposed for 3 h, 6 h and 16 h. Z304 hybridized only to M. simiae DNA but not to any of the other mycobacteria listed in Table 1b. None of the 106 tested non-mycobacterial DNA's listed in Table 2b cross-reacted with the M. simiae specific probe.

EXAMPLE 7.8

M. gordonae Specific Probe

The region 507–531 (Table 11) was selected with the following sequence: Z366: 5'-TCT GGG CGG CCG GTT GCT CAC CTT T-3' (SEQ ID NO: 15).

Z366 was end-labeled and hybridized as described in Example 6 against a filter on which 28 mycobacterial amplicons (26 different species) obtained with Z261 and Z212 were immobilized. Hybridization was performed at a temperature of 60° C. for 1–16 h, the washing temperature was 70° C. and the films were exposed for 3 h, 6 h and 16 h. Z366 hybridized only to M. gordonae DNA but not to any of the other mycobacteria listed in Table 1b. None of the 106 tested non-mycobacterial DNA's listed in Table 2b cross-reacted with the M. gordonae specific probe.

EXAMPLE 7.9

M. xenopi Specific Probe

The region 280–316 (Table 12) was selected with the following sequence:

Z309:5'-TCC GCG ATC GTC GGG CAT GAG AAG GCC CTC GCG TTC A-3' (SEQ ID NO: 18).

Z309 was end-labeled and hybridized as described in Example 6 against a filter on which 28 mycobacterial amplicons (26 different species) obtained with Z261 and Z212 were immobilized. Hybridization was performed at a temperature of 70° C. for 1–16 h, the washing temperature was 80° C. and the films were exposed for 3 h, 6 h and 16 h. Z309 hybridized only to M. xenopi DNA but not to any of the other mycobacteria listed in Table 1b. None of the 106 tested non-mycobacterial DNA's listed in Table 2b cross-reacted with the M. xenopi specific probe.

TABLE 1a

| Mycobacteria | ATCC | Z205/Z212[1] | Z261/Z212[2] | Z310–Z317[3] |
|---|---|---|---|---|
| M. acapulcensis | 14473 | + | + | + |
| M. africanum | 25420 | + | + | + |
| M. avium | 25291 | + | + | + |
| M. bovis | 19210 | + | + | + |
| M. bovis BCG*** | 1401 | + | + | + |
| M. brunense | 23434 | + | + | + |
| M. chelonae | 35752 | + | + | + |
| M. flavescens | DSM43219* | + | + | + |
| M. fortuitum | 6841 | + | + | + |
| M. gadium | 27726 | + | + | (+) |
| M. gastri | 15754 | + | + | + |
| M. gordonae | DSM610* | + | + | + |
| M. haemophilum | 29548 | + | + | (+) |
| M. intracellulare | DSM 43223* | + | + | + |
| M. kansasii | DSM43224* | + | + | + |
| M. marinum | 927 | + | + | + |
| M. nonchromogenicum | 19530 | + | + | + |
| M. obuense | 27023 | + | + | + |
| M. phlei | DSM750* | + | + | + |
| M. rhodesiae | 27024 | + | + | + |
| M. scrofulaceum | 19981 | + | + | + |
| M. simiae | 25275 | + | + | + |
| M. smegmatis | 14468 | + | + | + |

TABLE 1a-continued

| Mycobacteria | ATCC | Z205/Z212[1] | Z261/Z212[2] | Z310–Z317[3] |
|---|---|---|---|---|
| M. szulgai | 35799 | + | + | (+) |
| M. terrae | 15755 | + | + | + |
| M. triviale | 23292 | + | + | + |
| M. tuberculosis** | 1400 | + | + | + |
| M. tuberculosis | 27294 | + | + | + |
| M. xenopi | 19250 | + | + | + |

[1] Amplification with universal primer pair Z205/Z212
[2] Amplification with genus specific primer pair Z261/Z212
[3] Hybridization with genus specific pool of probes Z310–Z317
***Serum- und Impfinstitut, Bern, Switzerland
**clinical isolate
*DSM(Deutsche Sammlung von Mikroorganismen, Gottingen, FRG)

TABLE 1b

| Mycobacteria | ATCC | Hybridization with Species Specific Probes | | | | | | | | |
|---|---|---|---|---|---|---|---|---|---|---|
| | | A | B | C | D | E | F | G | H | I |
| M. acapulcensis | 14473 | – | – | – | – | – | – | – | – | – |
| M. africanum | 25420 | – | + | – | – | – | – | – | – | – |
| M. avium | 25291 | + | – | – | – | – | – | – | – | – |
| M. bovis | 19210 | – | + | – | – | – | – | – | – | – |
| M. bovis BCG*** | 1401 | – | + | – | – | – | – | – | – | – |
| M. brunense | 23434 | + | – | – | – | – | – | – | – | – |
| M. chelonai | 35752 | – | – | – | – | – | – | – | – | – |
| M. flavescens | DSM43219* | – | – | – | – | – | – | – | – | – |
| M. fortuitum | 6841 | – | – | – | – | – | – | – | + | – |
| M. gadium | 27726 | – | – | – | – | – | – | – | – | – |
| M. gastri | 15754 | – | – | – | – | – | – | – | – | – |
| M. gordonae | DSM610* | – | – | – | – | – | – | + | – | – |
| M. haemophilum | 29548 | – | – | – | – | – | – | – | – | – |
| M. intracellulare | DSM43223* | – | – | + | – | – | – | – | – | – |
| M. kansasii | DSM43224* | – | – | – | – | + | – | – | – | – |
| M. marinum | 927 | – | – | – | – | – | – | – | – | – |
| M. nonchromogenicum | 19530 | – | – | – | – | – | – | – | – | – |
| M. obuense | 27023 | – | – | – | – | – | – | – | – | – |
| M. phlei | DSM750* | – | – | – | – | – | – | – | – | – |
| M. rhodesiae | 27024 | – | – | – | – | – | – | – | – | – |
| M. scrofulaccum | 19981 | – | – | – | – | – | + | – | – | – |
| M. simiae | 25275 | – | – | – | + | – | – | – | – | – |
| M. smegmatis | 14468 | – | – | – | – | – | – | – | – | – |
| M. szulgai | 35799 | – | – | – | – | – | – | – | – | – |
| M. terrae | 15755 | – | – | – | – | – | – | – | – | – |
| M. triviale | 23292 | – | – | – | – | – | – | – | – | – |
| M. tuberculosis** | 1400 | – | + | – | – | – | – | – | – | – |
| M. tuberculosis | 27294 | – | + | – | – | – | – | – | – | – |
| M. xenopi | 19250 | – | – | – | – | – | – | – | – | + |

A: M. avium probe Z301
B: MTB probes Z337/Z336/Z302
C: M. intracellulare probe Z303
D: M. simiae probe Z304
E: M. kansasii probe Z340
F: M. scrofulaceum probe Z306
G: M. gordonae probe Z366
H: M. fortuitum probe Z369
I: M. xenopi probe Z309
***Serum- und Impfinstitut, Bern, Switzerland
**clinical isolate
*DSM (Deutsche Sammlung von Mikroorganismen, Gottingen, FRG)

TABLE 2a

| Non-mycobacterial Organisms | ATCC | Z205/Z212[1] | Z261/Z212[2] | Z310–Z317[3] |
|---|---|---|---|---|
| Acinetobacter calcoaceticus | 17945 | + | – | – |
| A. calcoaceticus | 23055 | + | – | – |
| Acinetobacter lwoffii | 15309 | + | – | – |
| Actinomyces bovis | DSM43014** | + | – | – |
| Actinomyces israelii | 12102 | + | – | – |
| Actinomyces meyeri | 35568 | + | – | – |
| Actinomyces odontolyticus | 17929 | + | – | – |
| Actinomyces viscosus | 15987 | + | – | – |
| Aeromonas hydrophila | 7966 | + | – | – |
| Agrobact. tumefaciens | 23308 | + | – | – |

TABLE 2a-continued

| Non-mycobacterial Organisms | ATCC | Z205/Z212[1] | Z261/Z212[2] | Z310–Z317[3] |
|---|---|---|---|---|
| Alcaligenes faecalis | 8750 | + | – | – |
| Arthrobacter globiformis | DSM20124** | + | – | – |
| Aspergillus flavus | RKI**** | + | – | – |
| Aspergillus fumigatus | RKI**** | + | – | – |
| Bacillus cereus | 27348 | + | – | – |
| Bacillus fragilis | RKI**** | + | – | – |
| Bacillus subtilis | 6633 | + | – | – |
| Bacteroides hetaitaomicron | RKI**** | + | – | – |
| Bifidobacterium dentium | DSM20084** | + | – | – |
| Bordatella parapertussis | DSM4922** | + | – | – |
| Branhamella catarrhalis | 8176 | + | – | – |
| Brevibact. epidermidis | DSM20660** | + | – | – |
| Campylobacter jejuni | 33560 | + | – | – |
| Campylobacter pylori | * | + | – | – |
| Candida albicans | 10231 | + | – | – |
| Candida glabrata | RKI**** | + | – | – |
| Citrobacter diversus | DSM4570** | + | – | – |
| Citrobacter freundii | 8090 | + | – | – |
| Clostridium difficile | RKI**** | + | – | – |
| Corynebact. diphteriae | 11913 | + | – | – |
| Corynebacter flavescens | 10340 | + | – | – |
| Corynebact. minutissimum | 23348 | + | – | – |
| C. pseudodiphtheriticum | RC181*** | + | – | – |
| C. pseudogenitalium | 33035 | + | – | – |
| Corynebacter striatum | 6940 | + | – | – |
| Corynebacter variabilis | 15753 | + | – | – |
| Corynebacter xerosis | 373 | + | – | – |
| E. coli | 25922 | + | – | – |
| Edwardsiella tarda | 15947 | + | (+) | – |
| Enterococcus avium | 14025 | + | – | – |
| Enterococcus durans | 19432 | + | – | – |
| Enterococcus faecalis | 19433 | + | – | – |
| Enterobacter cloacae | 13047 | + | – | – |
| Ewingella americana | DSM4580** | + | (+) | – |
| Flavobacterium odoratum | 4651 | + | – | – |
| Haemophilus influenzae | 9333 | + | – | – |
| Klebsiella pneumoniae | 13883 | + | (+) | – |
| Lactobacillus acidophilus | DSM20079** | + | – | – |
| Leishmania mexicana | RKI**** | + | – | – |
| Micrococcus luteus | RC9346*** | + | – | – |
| Neisseria lactamica | 23970 | + | – | – |
| Neisseria sicca | 9913 | + | – | – |
| Nocardia argentinensis | 31306 | + | – | – |
| Nocardia asteroides | 43005 | + | – | – |
| Nocardia brevicatena | 15333 | + | – | – |
| Peptostreptococcus anaerobius | RKI**** | + | – | – |
| Peptostreptococcus asaccharolyticus | RKI**** | + | – | – |
| Plesiomonas shigelloides | 14029 | + | – | – |
| Plasmodium falciparum 3D7 | RC*** | + | – | – |
| Prevotella livia | RKI**** | + | – | – |
| Prevotella intermedia | RKI**** | + | – | – |
| Propionbacterium acnes | DSM1897** | + | – | – |
| Proteus mirabilis | 12453 | + | – | – |
| Proteus vulgaris | 6380 | + | – | – |
| Pseudomonas acidovorans | RC15858*** | + | – | – |
| Pseudomonas aeruginosa | 10145 | + | – | – |
| Pseudomonas alcaligenes | 14909 | + | – | – |
| Pseudomonas fluorescens | 13525 | + | – | – |
| Pseudomonas putida | 12633 | + | – | – |
| Pseudomonas putrefaciens | DSM50426** | + | – | – |
| Rhodococcus equi | 6939 | + | – | – |
| Rhodococcus sputi | 29627 | + | – | – |
| Saccharomyces cerevisiae | RKI**** | + | – | – |
| Salmonella bongori | RC5951*** | + | – | – |
| Salmonella hautenea | RC5507*** | + | (+) | – |
| Salmonella salamae | RC5554*** | + | – | – |
| Salmonella typhimurium | 13311 | + | – | – |
| Serratia marcescens | 8100 | + | – | – |
| Shigella sonnei | 11060 | + | – | – |
| Staphylococcus aureus | 29213 | + | – | – |
| Staphylococcus capitis | 27840 | + | – | – |
| Staphylococcus cohnii | 29974 | + | – | – |
| Staphylococcus epidermidis | 12228 | + | – | – |

TABLE 2a-continued

| Non-mycobacterial Organisms | ATCC | Z205/Z212[1] | Z261/Z212[2] | Z310–Z317[3] |
|---|---|---|---|---|
| S. haemolyticus | 29970 | + | – | – |
| Staphylococcus hominis | 27844 | + | – | – |
| S. saprophyticus | 15305 | + | – | – |
| Staphylococcus simulans | 27848 | + | – | – |
| Staphylococcus warneri | 27838 | + | – | – |
| Staphylococcus xylosus | 29971 | + | – | – |
| Streptococcus agalactiae | 13813 | + | – | – |
| Streptococcus constellatus | 27823 | + | – | – |
| Streptococcus equi | 33398 | + | – | – |
| Streptococcus group A | RC17A4*** | + | – | – |
| Streptococcus mitis | 33399 | + | – | – |
| Streptococcus morbillorum | 27824 | + | – | – |
| Streptococcus mutans | 25175 | + | – | – |
| Streptococcus pneumoniae | 6301 | + | – | – |
| Streptococcus pneumoniae | 6303 | + | – | – |
| Streptococcus pyogenes | 19615 | + | – | – |
| Streptococcus salivarius | 7073 | + | – | – |
| Streptococcus sanguis | 10556 | + | – | – |
| Trypanosoma cruzei | RKI**** | + | – | – |
| Veillonella dispar | DSM20735** | + | – | – |
| Vibrio alginolyticus | DSM2171** | + | – | – |
| Yersinia enterocolitica | 9610 | + | – | – |
| Y. pseudotuberculosis | 907 | + | – | – |

[1] Amplification with universal primer pair Z205/Z212
[2] Amplification with genus specific primer pair Z261/Z212
[3] Hybridization with genus specific pool of probes Z310–Z317
*clinical isolate
**DSM (Deutsche Sammlung von Mikroorganismen, Gottingen, FRG
***RC (Roche collection)
****RKI (Robert Koch Institute, Berlin, FRG)

TABLE 2b

| Non-mycobacterial Organisms | ATCC | Hybridization with Species Specific Probes | | | | | | | | |
|---|---|---|---|---|---|---|---|---|---|
| | | A | B | C | D | E | F | G | H | I |
| Acinetobact. calc. | 17945 | – | – | – | – | – | – | – | – | – |
| A. calcoaceticus | 23055 | – | – | – | – | – | – | – | – | – |
| Acinetobacter lwoffii | 15309 | – | – | – | – | – | – | – | – | – |
| Actinomyces bovi | DSM43014** | – | – | – | – | – | – | – | – | – |
| Actinomyces israelii | 12102 | – | – | – | – | – | – | – | – | – |
| Actinomyces meyeri | 35568 | – | – | – | – | – | – | – | – | – |
| Actinomyces odont. | 17929 | – | – | – | – | – | – | – | – | – |
| Actinomyces viscosus | 15987 | – | – | – | – | – | – | – | – | – |
| Acromonas hydrophila | 7966 | – | – | – | – | – | – | – | – | – |
| Agrobact. tumefaciens | 23308 | – | – | – | – | – | – | – | – | – |
| Alcaligenes faecalis | 8750 | – | – | – | – | – | – | – | – | – |
| Arthrobact. globiformis | DSM20124** | – | – | – | – | – | – | – | – | – |
| Aspergillus flavus | RKI**** | – | – | – | – | – | – | – | – | – |
| Aspergillus fumigatus | RKI**** | – | – | – | – | – | – | – | – | – |
| Bacillus cereus | 27348 | – | – | – | – | – | – | – | – | – |
| Bacillus fragilis | RKI**** | – | – | – | – | – | – | – | – | – |
| Bacillus subtilis | 6633 | – | – | – | – | – | – | – | – | – |
| Bacteroides hetaitaomicron | RKI**** | – | – | – | – | – | – | – | – | – |
| Bifidobact. dentium | DSM20084** | – | – | – | – | – | – | – | – | – |
| Bordatella parapert. | DSM4922** | – | – | – | – | – | – | – | – | – |
| Branhamella catarrh. | 8176 | – | – | – | – | – | – | – | – | – |
| Brevibact. epidermidis | DSM20660** | – | – | – | – | – | – | – | – | – |
| Campylobacter jejuni | 33560 | – | – | – | – | – | – | – | – | – |
| Campylobacter pylori | * | – | – | – | – | – | – | – | – | – |
| Candida albicans | 10231 | – | – | – | – | – | – | – | – | – |
| Candida glabrata | RKI**** | – | – | – | – | – | – | – | – | – |
| Citrobacter diversus | DSM4570** | – | – | – | – | – | – | – | – | – |
| Citrobacter freundii | 8090 | – | – | – | – | – | – | – | – | – |
| Clostridium difficile | RKI**** | – | – | – | – | – | – | – | – | – |
| Corynebact. diphteriae | 11913 | – | – | – | – | – | – | – | – | – |
| Corynebact. flavescens | 10340 | – | – | – | – | – | – | – | – | – |
| Corynebact. minutiss. | 23348 | – | – | – | – | – | – | – | – | – |
| C. pseudodipht. | RC181*** | – | – | – | – | – | – | – | – | – |
| C. pseudogenitalium | 33035 | – | – | – | – | – | – | – | – | – |
| Corynebacter striatum | 6940 | – | – | – | – | – | – | – | – | – |

TABLE 2b-continued

| Non-mycobacterial Organisms | ATCC | Hybridization with Species Specific Probes | | | | | | | | |
|---|---|---|---|---|---|---|---|---|---|---|
| | | A | B | C | D | E | F | G | H | I |
| *Corynebacter variabilis* | 15753 | − | − | − | − | − | − | − | − | − |
| *Corynebacter xerosis* | 373 | − | − | − | − | − | − | − | − | − |
| *E. coli* | 25922 | − | − | − | − | − | − | − | − | − |
| *Edwardsiella tarda* | 15947 | − | − | − | − | − | − | − | − | − |
| *Enterococcus avium* | 14025 | − | − | − | − | − | − | − | − | − |
| *Enterococcus durans* | 19432 | − | − | − | − | − | − | − | − | − |
| *Enterococcus faecalis* | 19433 | − | − | − | − | − | − | − | − | − |
| *Enterobacter cloacae* | 13047 | − | − | − | − | − | − | − | − | − |
| *Ewingella americana* | DSM4580** | − | − | − | − | − | − | − | − | − |
| *Flavobact. odoratum* | 4651 | − | − | − | − | − | − | − | − | − |
| *Haemophilus infl.* | 9333 | − | − | − | − | − | − | − | − | − |
| *Klebsiella pneumoniae* | 13883 | − | − | − | − | − | − | − | − | − |
| *Lactobacillus acidoph.* | DSM20079** | − | − | − | − | − | − | − | − | − |
| *Leishmania mexicana* | RKI**** | − | − | − | − | − | − | − | − | − |
| *Micrococcus luteus* | RC9346*** | − | − | − | − | − | − | − | − | − |
| *Neisseria lactamica* | 23970 | − | − | − | − | − | − | − | − | − |
| *Neisseria sicca* | 9913 | − | − | − | − | − | − | − | − | − |
| *Nocardia argent.* | 31306 | − | − | − | − | − | − | − | − | − |
| *Nocardia asteroides* | 43005 | − | − | − | − | − | − | − | − | − |
| *Nocardia brevicatena* | 15333 | − | − | − | − | − | − | − | − | − |
| *Peptostreptococcus anaerobius* | RKI**** | − | − | − | − | − | − | − | − | − |
| *Peptostreptococcus asaccharolyticus* | RKI**** | − | − | − | − | − | − | − | − | − |
| *Plesiomonas shigell.* | 14029 | − | − | − | − | − | − | − | − | − |
| *Plasmodium falciparum 3D7* | RC*** | − | − | − | − | − | − | − | − | − |
| *Prevotella livia* | RKI**** | − | − | − | − | − | − | − | − | − |
| *Prevotella intermedia* | RKI**** | − | − | − | − | − | − | − | − | − |
| *Propionbact. acnes* | DSM1897** | − | − | − | − | − | − | − | − | − |
| *Proteus mirabilis* | 12453 | − | − | − | − | − | − | − | − | − |
| *Proteus vulgaris* | 6380 | − | − | − | − | − | − | − | − | − |
| *Pseudom. acidovorans* | RC15858*** | − | − | − | − | − | − | − | − | − |
| *Pseudom. aeruginosa* | 10145 | − | − | − | − | − | − | − | − | − |
| *Pseudom. alcaligenes* | 14909 | − | − | − | − | − | − | − | − | − |
| *Pseudom. fluorescens* | 13525 | − | − | − | − | − | − | − | − | − |
| *Pseudomonas putida* | 12633 | − | − | − | − | − | − | − | − | − |
| *Pseudom. putrefac.* | DSM50426** | − | − | − | − | − | − | − | − | − |
| *Rhodococcus equi* | 6939 | − | − | − | − | − | − | − | − | − |
| *Rhodococcus sputi* | 29627 | − | − | − | − | − | − | − | − | − |
| *Saccharomyces cervisiae* | RKI**** | − | − | − | − | − | − | − | − | − |
| *Salmonella bongori* | RC5951*** | − | − | − | − | − | − | − | − | − |
| *Salmonella hautenea* | RC5507*** | − | − | − | − | − | − | − | − | − |
| *Salmonella salamae* | RC5554*** | − | − | − | − | − | − | − | − | − |
| *Salmonella typh.* | 13311 | − | − | − | − | − | − | − | − | − |
| *Serratia marcescens* | 8100 | − | − | − | − | − | − | − | − | − |
| *Shigella sonnei* | 11060 | − | − | − | − | − | − | − | − | − |
| *Staphylococcus aureus* | 29213 | − | − | − | − | − | − | − | − | − |
| *Staphylococcus capitis* | 27840 | − | − | − | − | − | − | − | − | − |
| *Staphylococcus cohnii* | 29974 | − | − | − | − | − | − | − | − | − |
| *S. epidermidis* | 12228 | − | − | − | − | − | − | − | − | − |
| *S. haemolyticus* | 29970 | − | − | − | − | − | − | − | − | − |
| *S. hominis* | 27844 | − | − | − | − | − | − | − | − | − |
| *S. saprophyticus* | 15305 | − | − | − | − | − | − | − | − | − |
| *S. simulans* | 27848 | − | − | − | − | − | − | − | − | − |
| *S. warneri* | 27838 | − | − | − | − | − | − | − | − | − |
| *Staph. xylosus* | 29971 | − | − | − | − | − | − | − | − | − |
| *Streptococcus agalact.* | 13813 | − | − | − | − | − | − | − | − | − |
| *Streptococcus constel.* | 27823 | − | − | − | − | − | − | − | − | − |
| *Streptococcus equi* | 33398 | − | − | − | − | − | − | − | − | − |
| *Streptococcus group A* | RC17A4*** | − | − | − | − | − | − | − | − | − |
| *Streptococcus mitis* | 33399 | − | − | − | − | − | − | − | − | − |
| *Streptococcus morbil.* | 27824 | − | − | − | − | − | − | − | − | − |
| *Streptococcus mutans* | 25175 | − | − | − | − | − | − | − | − | − |
| *Streptococcus pneum.* | 6301 | − | − | − | − | − | − | − | − | − |
| *Streptococcus pneum.* | 6303 | − | − | − | − | − | − | − | − | − |
| *Streptococcus pyogenes* | 19615 | − | − | − | − | − | − | − | − | − |
| *Streptococcus saliv.* | 7073 | − | − | − | − | − | − | − | − | − |
| *Streptococcus sanguis* | 10556 | − | − | − | − | − | − | − | − | − |
| *Trypanosoma Cruzei* | RKI**** | − | − | − | − | − | − | − | − | − |
| *Veillonella dispar* | DSM20735** | − | − | − | − | − | − | − | − | − |
| *Vibrio alginolyticus* | DSM2171** | − | − | − | − | − | − | − | − | − |
| *Yersinia enterocolitica* | 9610 | − | − | − | − | − | − | − | − | − |

TABLE 2b-continued

| Non-mycobacterial Organisms | ATCC | Hybridization with Species Specific Probes | | | | | | | | |
|---|---|---|---|---|---|---|---|---|---|---|
| | | A | B | C | D | E | F | G | H | I |
| *Y. pseudotuberculosis* | 907 | − | − | − | − | − | − | − | − | − |

A: *M. avium* probe Z301
B: MTB probes Z337/Z336/Z302
C: *M. intracellulare* probe Z303
D: *M. simiae* probe Z304
E: *M. kansasii* probe Z340
F: *M. scrofulaceum* probe Z306
G: *M. gordonae* probe Z366
H: *M. fortuitum* probe Z369
I: *M. xenopi* probe Z309
*clinical isolate
**DSM (Deutsche Sammlung von Mikroorganismen, Gottingen, FRG)
***RC (Roche collection)
****RKI (Robert Koch Institute, Berlin, FRG)

TABLE 3

Sequencing Primers

| All Mycobacteria | | SEQ ID NO: | Position |
|---|---|---|---|
| *N. asteroides* | | | |
| Z205: | 5'-AGC TTC ACC ACA GCA AGC ACC A-3' | 1 | 188–209 |
| Z256: | 5'-CAC WCS ATC TGG TGG AAG AAC CT-3' | 24 | 337–359 |
| Z243: | 5'-ACG GYG GYG ACA AGC CGA CCG G-3' | 25 | 368–389 |
| Z244: | 5'-GTC TGS TGG TCG TAR ASC TGG A-3' | 26 | 551–539 |
| Z212: | 5'-TCG KCC CAG TTC ACG ACR TTC CA-3' | 2 | 678–655 |
| *C. diphteriae* | | | |
| Z205: | see above | | |
| Z257: | 5'-GGA TTT GGC TTT CAA CTT GGG-3' | 27 | 306–326 |
| Z245: | 5'-GGC GAG CCA ACC GGC GCT TTG G-3' | 28 | 376–397 |
| Z212: | see above | | |
| *C. pseudo-diphtheriticum* | | | |
| Z258: | 5'-GAA GAA CCT GAG CCT TAA CGG T-3' | 29 | 351–372 |
| Z247: | 5'-GAG CCA ACC GGT GAG CTA GCC-3' | 30 | 379–399 |
| Z212: | see above | | |
| *A. viscosus* | | | |
| Z246: | 5'-GAA GAA CCT CTC CCC CAA CGG C-3' | 31 | 351–372 |
| Z244: | see above | | |
| Z212: | see above | | |

TABLE 4

*Mycobacterium tuberculosis* SOD gene for super oxide dismutase

```
  1 . . . . . . . . . .  . . . . . . . . . .  . . . . . . . . . .  . . . . . . . . . .  . . . . . . . . . .
 51 . . . . . . . . . .  . . . . . . . . . .  . . . . . . . . . .  . . . . . . . . . .  . . . . . . . . . .
101 . . . . . . . . . .  . . . . . . . . . .  . . . . . . . . . .  . . . . . . . . . .  . . . . . . . . . .
151 . . . . . . . . . .  . . . . . . . . . .  . . . . . . . . . .  . . . . . AGC        TTCACCACAG
201 CAAGCACCAC           GCCACCTACG           TAAAGGGCGC           CAATGACGCC           GTCGCCAAAC
251 TCGAAGAGGC           GCGCGCCAAG           GAAGATCACT           CAGCGATCTT           GCTGAACGAA
301 AAGAATCTAG           CTTTCAACCT           CGCCGGCCAC           GTCAATCACA           CCATCTGGTG
351 GAAGAACCTG           TCGCCTAACG           GTGGTGACAA           GCCCACCGGC           GAACTCGCCG
401 CAGCCATCGC           CGACGCGTTC           GGTTCGTTCG           ACAAGTTCCG           TGCGCAGTTC
451 CACGCGGCCG           CTACCACCGT           GCAGGGGTCG           GGCTGGGCGG           CACTGGGCTG
501 GGACACACTC           GGCAACAAGC           TGCTGATATT           CCAGGTTTAC           GACCACCAGA
551 CGAACTTCCC           GCTAGGCATT           GTTCCGCTGC           TGCTGCTCGA           CATGTGGGAA
601 CACGCCTTCT           ACCTGCAGTA           CAAGAACGTC           AAAGTCGACT           TTGCCAAGGC
651 GTTTTGGAAC           GTCGTGAACT           GGGCCGAT . .         . . . . . . . . . .  . . . . . . . . . .
701 . . . . . . . . . .  . . . . . . . . . .  . . . . . . . . . .  . . . . . . . . . .  . . . . . . . . . .
751 . . . . . . . . . .  . . . . . . . . . .  . . . . . . . . . .  . . . . . . . . . .  . . . . . . . . . .
```

TABLE 5

Mycobacterium avium SOD gene for super oxide dismutase

| | | | | | |
|---|---|---|---|---|---|
| 1 | .......... | .......... | .......... | .......... | .......... |
| 51 | .......... | .......... | .......... | .......... | .......... |
| 101 | .......... | .......... | .......... | .......... | .......... |
| 151 | .......... | .......... | .......... | .....AGC | TTCACCACAG |
| 201 | CAAGCACCAC | GCCACCTACG | TCAAAGGCGT | GAACGACGCT | CTTGCCAAGC |
| 251 | TCGAAGAGGC | CCGCGCCAAC | GAGGACCACG | CTGCGATCTT | CCTGAACGAA |
| 301 | AAGAACCTCG | CCTTCCACCT | GGGCGGCCAC | GTCAACCACT | CGATCTGGTG |
| 351 | GAAGAACCTG | TCGCCGGACG | GCGGTGACAA | GCCCACCGGT | GAGCTGGCCG |
| 401 | CCGCGATCGA | CGACGCGTTC | GGGTCCTTCG | ACAAGTTCCG | AGCGCAATTC |
| 451 | AGCGCCGCCG | CCAACGGCCT | GCAGGGCTCC | GGCTGGGCGG | TGCTGGGCTA |
| 501 | TGACACCCTG | GGCAGCCGGT | TGCTGACCTT | CCAGCTCTAC | GACCAGCGGG |
| 551 | CCAACGTCCC | GCTGGGCATC | ATCCCGCTTC | TGCAGGTCGA | CATGTGGGAG |
| 601 | CACGCGTTCT | ACCTGCAGTA | CAAGAACGTC | AAGGCGGACT | ACGTCAAGGC |
| 651 | GTTCTGGAAC | GTCGTGAACT | GGGCCGAT.. | .......... | .......... |
| 701 | .......... | .......... | .......... | .......... | .......... |
| 751 | .......... | .......... | .......... | .......... | .......... |

TABLE 6

Mycobacterium intracellulare SOD gene for super oxide dismutase

| | | | | | |
|---|---|---|---|---|---|
| 1 | .......... | .......... | .......... | .......... | .......... |
| 51 | .......... | .......... | .......... | .......... | .......... |
| 101 | .......... | .......... | .......... | .......... | .......... |
| 151 | .......... | .......... | .......... | .....AGC | TTCACCACAG |
| 201 | CAAGCACCAC | GCCACCTACG | TCAAAGGCGT | GAACGACGCT | CTGTCCAAGC |
| 251 | TCGAAGAGGC | CCGTGCCAAC | GAAGATCACG | CTGCGATCTT | CCTGAACGAA |
| 301 | AAGAACCTGG | CCTTTCACCT | GGGCGGCCAC | GTCAACCACT | CCATCTGGTG |
| 351 | GAAGAACCTG | TCGCCGGACG | GCGGCGACAA | GCCGACCGGC | GAATTGGCCG |
| 401 | CCGCGATCGA | CGACGCCTTC | GGATCCTTCG | ACCGGTTCCG | CGCGCAGTTC |
| 451 | AGCGCGGCCG | CCAACGGCCT | GCAGGGGTCG | GGCTGGGCGG | TGCTGGGCTA |
| 501 | CGACACCCTC | GGCAACCGGC | TGCTGACCTT | CCAGCTCTAC | GACCAGCAGG |
| 551 | CCAACGTGCC | GCTGGGCATC | ATTCCGCTGC | TGCAGGTCGA | CATGTGGGAG |
| 601 | CACGCTTTCT | ACCTGCAGTA | CAAGAACGTC | AAGGCGGACT | ACGTCAAGGC |
| 651 | GTTCTGGAAC | GTCGTGAACT | GGGACGAT.. | .......... | .......... |
| 701 | .......... | .......... | .......... | .......... | .......... |
| 751 | .......... | .......... | .......... | .......... | .......... |

TABLE 7

Mycobacterium scrofulaceum SOD gene for super oxide dismutase

| | | | | | |
|---|---|---|---|---|---|
| 1 | .......... | .......... | .......... | .......... | .......... |
| 51 | .......... | .......... | .......... | .......... | .......... |
| 101 | .......... | .......... | .......... | .......... | .......... |
| 151 | .......... | .......... | .......... | .....AGC | TTCACCACAG |
| 201 | CAAGCACCAC | GCCACGTACG | TCAAGGGCGT | GAACGACGCC | GTCGCCAAAC |
| 251 | TCCAAGAGGC | ACGCGCCAAT | GACGACCACG | CCGCGATCTT | CCTGAACGAA |
| 301 | AAGAACCTGG | CGTTCCACCT | CGGCGGCCAC | GTGAACCACT | CGATCTGGTG |
| 351 | GAAGAACCTC | TCGCCGGACG | GCGGCGACAA | GCCGACCGGA | GAACTGGCCG |
| 401 | CCGCGATCGA | TGACGCGTTC | GGATCGTTCG | ACAAATTCCG | CGCCCAGTTC |
| 451 | AGTGCGGCCG | CCAACGGCCT | GCAGGGTTCG | GGCTGGGCGG | TGCTGGGCTA |
| 501 | TGACACACTC | GGCAGCAGGC | TGCTCACCTT | CCAGCTTTAC | GACCAGCAGG |
| 551 | CCAACGTCCC | GCTCGGCATC | ATTCCGCTGC | TGCAGGTCGA | CATGTGGGAG |
| 601 | CACGCCTTTT | ACTTGCAGTA | CAAGAACGTC | AAGGCCGACT | ACGTCAAGGC |
| 651 | CTTCTGGAAT | GTCGTGAACT | GGGCCGAG.. | .......... | .......... |
| 701 | .......... | .......... | .......... | .......... | .......... |
| 751 | .......... | .......... | .......... | .......... | .......... |

TABLE 8

Mycobacterium kansasii SOD gene for super oxide dismutase

| | | | | | |
|---|---|---|---|---|---|
| 1 | .......... | .......... | .......... | .......... | .......... |
| 51 | .......... | .......... | .......... | .......... | .......... |
| 101 | .......... | .......... | .......... | .......... | .......... |
| 151 | .......... | .......... | .......... | .....AGC | TTCACCACAG |
| 201 | CAAGCACCAC | GCCACCTACG | TCAAGGGCGC | CAACGATGCG | GTCGCCAAAC |
| 251 | TCGAAGAGGC | GCGCGCCAAG | GAAGACCACT | CGGCGATCTT | GCTGAACGAG |
| 301 | AAGAACTTGG | CCTTCAACCT | CGCCGGCCAC | GTCAACCACA | CGATCTGGTG |
| 351 | GAAGAACCTT | TCTCCCAACG | GAGGCGACAA | GCCGACCGGC | GAACTCGCCG |
| 401 | CGGCCATCGA | CGAGGCGTTC | GGGTCCTTCG | ACAAGTTTCG | TGCCCAATTC |

TABLE 8-continued

Mycobacterium kansasii SOD gene for super oxide dismutase

| | | | | | |
|---|---|---|---|---|---|
| 451 | CACGCCGCCG | CCACCACGGT | GCAGGGGTCG | GGCTGGGCGG | CGCTGGGCTG |
| 501 | GGACACTCTC | GGCAACAAGC | TGCTGATATT | CCAGGTCTAC | GACCACCAGA |
| 551 | CGAACTTTCC | ACTCGGAATC | ATTCCGTTAC | TGCTGCTCGA | CATGTGGGAA |
| 601 | CACGCTTTCT | ACCTCCAGTA | CAAGAATGTC | AAGGTCGACT | TCGCCAAAGC |
| 651 | ATTCTGGAAC | GTCGTGAACT | GGGACGAT.. | .......... | .......... |
| 701 | .......... | .......... | .......... | .......... | .......... |
| 751 | .......... | .......... | .......... | .......... | .......... |

TABLE 9

Mycobacterium fortuitum SOD gene for super oxide dismutase

| | | | | | |
|---|---|---|---|---|---|
| 1 | .......... | .......... | .......... | .......... | .......... |
| 51 | .......... | .......... | .......... | .......... | .......... |
| 101 | .......... | .......... | .......... | .......... | .......... |
| 151 | .......... | .......... | .......... | .....AGC | TTCACCACAG |
| 201 | CAAGCACCAC | GCCGCGTACG | TCAAGGGCGT | CAACGACGCC | GTGGCCAAGC |
| 251 | TCGATGAGGC | GCGGGCCAAC | GGTGACCACG | CGGCGATCTT | CCTCAACGAG |
| 301 | AAGAACCTGG | CGTTCCATCT | CGGCGGCCAC | GTGAACCACT | CGATCTGGTG |
| 351 | GAAGAACCTG | TCCCCCAACG | GTGGTGACAA | GCCGACGGGC | GATCTGGCCG |
| 401 | CGGCGATCGA | CGATCAGTTC | GGCTCGTTCG | ACAAGTTCCA | GGCGCAGTTC |
| 451 | ACCGCCGCCG | CCAACGGGCT | GCAGGGCTCG | GGCTGGGCCG | TGCTCGGCTA |
| 501 | CGACAGCCTG | GGCGATCGGC | TGCTGACCTT | CCAGCTCTAC | GACCAGCAGG |
| 551 | CCAACGTGCC | GCTCGGCATC | ATCCCGCTGC | TCCAGGTCGA | CATGTGGGAG |
| 601 | CACGCCTTCT | ACCTGCAGTA | CAAGAACGTC | AAGGCCGACT | ACGTCAAGGC |
| 651 | GTTCTGGAAA | GTCGTGAACT | GGGACGAT.. | .......... | .......... |
| 701 | .......... | .......... | .......... | .......... | .......... |
| 751 | .......... | .......... | .......... | .......... | .......... |

TABLE 10

Mycobacterium simiae SOD gene for super oxide dismutase

| | | | | | |
|---|---|---|---|---|---|
| 1 | .......... | .......... | .......... | .......... | .......... |
| 51 | .......... | .......... | .......... | .......... | .......... |
| 101 | .......... | .......... | .......... | .......... | .......... |
| 151 | .......... | .......... | .......... | .....AGC | TTCACCACAG |
| 201 | CAAGCACCAT | GCGACGTACG | TCAAGGGTTT | GAACGACGCC | ATTGCCAAGC |
| 251 | TTGAAGAGGC | GCGGGCCAAC | GACGACCATG | CCGCGATCTT | CTTGAACGAG |
| 301 | AAGAATCTGG | CATTCCACCT | CGGTGGCCAC | GTCAACCACT | CCATCTGGTG |
| 351 | GAAAAACCTG | TCCCCGAACG | GCGGAGACAA | GCCGACCGGA | GATCTCGCCG |
| 401 | CCGCCATCGA | CGACGCCTTC | GGTTCGTTCG | ACAAGTTCCA | CGCACAGTTC |
| 451 | AGCGCCGCCG | CCAACGGCTT | GCAGGGCTCG | GGCTGGGCGG | TACTCGGCTA |
| 501 | CGACACCCGG | GGCGACCGAC | TGCTGACCTT | CCAGCTTTAC | GACCAGCAGG |
| 551 | CCAACGTCCC | GCTGGGCATC | ATCCCGCTGC | TCAGGTCGA | CATGTGGGAG |
| 601 | CACGCCTTCT | ACCTGCAGTA | CAAGAACGTC | AAGGCGGACT | ACGTCAAGGC |
| 651 | GTTCTGGAAC | GTCGTGAACT | GGGACGAT.. | .......... | .......... |
| 701 | .......... | .......... | .......... | .......... | .......... |
| 751 | .......... | .......... | .......... | .......... | .......... |

TABLE 11

Mycobacterium gordonae SOD gene for super oxide dismutase

| | | | | | |
|---|---|---|---|---|---|
| 1 | .......... | .......... | .......... | .......... | .......... |
| 51 | .......... | .......... | .......... | .......... | .......... |
| 101 | .......... | .......... | .......... | .......... | .......... |
| 151 | .......... | .......... | .......... | .....AGC | TTCACCACAG |
| 201 | CAAGCACCAC | GCCACCTACG | TCAAAGGCGT | CAACGACGCG | GTCGCCAAGC |
| 251 | TGGAAGAAGC | GCGCGCCAAA | GGCGACCACT | CGGCCATCTT | TTTGAACGAG |
| 301 | AAGAACCTGG | CCTTCCACCT | GGGCGGTCAC | GTCAACCACT | CCATCTGGTG |
| 351 | GAAGAACCTG | TCGCCGGACG | GCGGCGACAA | GCCGACCGGT | GACCTGGCCG |
| 401 | CCGCGATCGA | CGACCAGTTC | GGCTCGTTCG | ACAAGTTCCA | GGCTCAGTTC |
| 451 | AGCGCCGCCG | CAAACGGCCT | ACAGGGCTCG | GGCTGGGCGG | TGCTCGGCTA |
| 501 | CGACACTCTG | GGCGGCCGGT | TGCTCACCTT | TCAGCTCTAC | GACCAGCAGG |
| 551 | CCAATGTCCC | GCTCGGTGTC | ATTCCGCTGT | TGCAGGTCGA | CATGTGGGAG |
| 601 | CACGCCTTCT | ACCTGCAGTA | CAAGAACGTC | AAGGCCGACT | ACGTCAAGGC |
| 651 | CTTCTGGAAC | GTCGTGAACT | GGGACGAC.. | .......... | .......... |
| 701 | .......... | .......... | .......... | .......... | .......... |
| 751 | .......... | .......... | .......... | .......... | .......... |

TABLE 12

Mycobacterium xenopi SOD gene for super oxide dismutase

| | | | | | |
|---|---|---|---|---|---|
| 1 | .......... | .......... | .......... | .......... | .......... |
| 51 | .......... | .......... | .......... | .......... | .......... |
| 101 | .......... | .......... | .......... | .......... | .......... |
| 151 | .......... | .......... | .......... | .....AGC | TTCACCACAG |
| 201 | CAAGCACCAC | GCGACGTACG | TCAAAGGCGC | CAACGACGCG | CTCGCCAAGC |
| 251 | TGGAGGAGGC | GCGCGCCAAA | GACGATCATT | CCGCGATCGT | CGGGCATGAG |
| 301 | AAGGCCCTCG | CGTTCAACCT | GGCCGGCCAT | GTCAATCACT | GCCTGTGGTG |
| 351 | GAAGAACCTG | TCCCCCAACG | GCGGTGACAA | GCCGACCGGC | GAATTGGCCG |
| 401 | CCGCCATCGA | CGACGCGTTC | GGCTCGTTCG | ACAAGTTCCG | CGCCCAGTTC |
| 451 | ACCGCGGCCG | CCACGACCGT | GCAGGGGTCG | GGCTGGGCGG | CACTCGGCTG |
| 501 | GGACAGCCTG | GGTGGCAAGC | TCCTGGTGTT | CCAGGTCTAC | GACCACCAGT |
| 551 | CCAACTTCCC | GCTCGGGATC | GTCCCCCTGC | TGGTGCTCGA | CATGTGGGAG |
| 601 | CACGCCTTCT | ACCTGCAGTA | CAAGAATGTC | AAGGCTGACT | TCGCCAAAGC |
| 651 | ATTCTGGAAC | GTCGTGAACT | GGGCCGAT.. | .......... | .......... |
| 701 | .......... | .......... | .......... | .......... | .......... |
| 751 | .......... | .......... | .......... | .......... | .......... |

TABLE 13

Corynebacterium diphteriae SOD gene for super oxide dismutase

| | | | | | |
|---|---|---|---|---|---|
| 1 | .......... | .......... | .......... | .......... | .......... |
| 51 | .......... | .......... | .......... | .......... | .......... |
| 101 | .......... | .......... | .......... | .......... | .......... |
| 151 | .......... | .......... | .......... | .....AGC | TTCACCACAG |
| 201 | CAAGCACCAC | GCTAACTACG | TGAACGGTGC | AAATACTGCT | CTTGAGAAGC |
| 251 | TGCAAAAGGC | TCGCGAGAAC | GGTGAGATCG | GTGCTGTTGT | CACCGCTTTG |
| 301 | TCCAAGGATT | TGGCTTTCAA | CTTGGGTGGC | CACACCAACC | ACTCCATCTT |
| 351 | CTGGAAGAAC | CTCTCCCCTA | ACGGTGGCGG | CGAGCCAACC | GGCGCTTTGG |
| 401 | CTGAGGCAAT | TGCCAAGGAG | TTCGGTTCTT | TTGAGAAGTT | CAAGGATCAC |
| 451 | TTCTCTGCTG | CGGCTCTTGG | TCTGCAGGGT | TCCGGCTGGG | CTGTTCTCGG |
| 501 | CTACGATCAC | ATCGGTGGCC | GTCTGGTTAT | CGAGCAGCTC | ACTGACCAGC |
| 551 | AGGGCAACAT | CTCCGCTAAC | CTGACCCCAC | TTCTTATGCT | CGATATGTGG |
| 601 | GAGCACGCTT | TCTACCTTCA | GTACAAGAAC | GTGAAGGCTG | ACTACGTCAA |
| 651 | GGCTGTGTGG | AACGTCGTGA | ACTGGGACGA | TG........ | .......... |
| 701 | .......... | .......... | .......... | .......... | .......... |
| 751 | .......... | .......... | .......... | .......... | .......... |

TABLE 14

C. pseudodiphteriticum SOD gene for super oxide dismutase

| | | | | | |
|---|---|---|---|---|---|
| 1 | .......... | .......... | .......... | .......... | .......... |
| 51 | .......... | .......... | .......... | .......... | .......... |
| 101 | .......... | .......... | .......... | .......... | .......... |
| 151 | .......... | .......... | .......... | .....AGC | TTCACCACAG |
| 201 | CAAGCACCAC | AACACTTACG | TGCAGGGTGC | TAACGCAGCT | TTGGACGCTC |
| 251 | TGGAAGAAGA | GCGCAACGGC | GAAGCCAACC | CAGACCGCAT | CCGTGCGCTG |
| 301 | TCCAAGAACT | TGGCTTTCCA | ACCTGGCCAC | ACCAACCACT | CCATCTTCTG |
| 351 | GAAGAACCTG | AGCCCTAACG | GTGGCGGCGA | GCCAACCGGT | GAGCTAGCAG |
| 401 | AGGCTATCGA | CCGCGACTTT | GGTTCCTTCG | AGAAGTTCAA | GGCGCACTTC |
| 451 | TCCGCAGCAG | CACTCGGCCT | GCAGGGTTCC | GGCTGGGCCG | TGCTGGGTTA |
| 501 | CGACCACATT | GCTGGTCGCC | TGCTCGTTGA | GCAGCTGACC | GACCAGCAGG |
| 551 | GCAACACTTC | CGTGAACTTC | ACCCCACTTC | TGATGCTGGA | TATGTGGGAG |
| 601 | CACGCTTTCT | ACCTGCAGTA | CAAGAACGTC | AAGCCTGATT | ACGTCAAGGC |
| 651 | TGTCTGGAAC | GTCGTGAACT | GGGACGAT.. | .......... | .......... |
| 701 | .......... | .......... | .......... | .......... | .......... |

TABLE 15

Nocardia asteroides SOD gene for super oxide dismutase

| | | | | | |
|---|---|---|---|---|---|
| 1 | .......... | .......... | .......... | .......... | .......... |
| 51 | .......... | .......... | .......... | .......... | .......... |
| 101 | .......... | .......... | .......... | .......... | .......... |
| 151 | .......... | .......... | .......... | .....AGC | TTCACCACAG |
| 201 | CAAGCACCAC | GCCGCCTACG | TCGCCGGTGC | CAACACGGCA | CTGGAGAAGC |
| 251 | TGGAAGCCGC | CCGTGAGGCC | GGCGATCACA | GCGCGATCTT | CCTGCACGAG |
| 301 | AAGAACCTCG | CGTTCCACCT | CGGCGGACAC | GTCAACCACT | CCATCTGGTG |
| 351 | GAAGAACCTG | TCCCCCAACG | GTGGCGACAA | GCCGGTCGGC | GAGCTGGCCG |
| 401 | CGGCCATCGA | CGACCAGTTC | GGTTCGTTCG | ACAAGTTCCG | CGCGCAGTTC |
| 451 | ACCGCCGCGC | CAACGGCCTG | CAGGGCTCGG | GCTGGGCGGT | GCTCGGTTAC |

TABLE 15-continued

Nocardia asteroides SOD gene for super oxide dismutase

| 501 | GACACCCTCG | GCCAGAAGCT | GCTGACCTTC | CAGCTCTACG | ACCAGCAGGC |
|-----|------------|------------|------------|------------|------------|
| 551 | CAACGTGCCG | CTGGGCATCA | TCCCGCTGCT | CCAAGTCGAC | ATGTGGGAGC |
| 601 | ACGCCTTCTA | CCTGCAGTAC | AAGAACGTCA | AGGCCGACTA | CGTGACCGCG |
| 651 | TTGTGGAACG | TCGTGCACTG | GGCCGAT... | .......... | .......... |
| 701 | .......... | .......... | .......... | .......... | .......... |
| 751 | .......... | .......... | .......... | .......... | .......... |

TABLE 16

Actinomyces viscosus SOD gene for super oxide dismutase

| 1 | .......... | .......... | .......... | .......... | .......... |
|-----|------------|------------|------------|------------|------------|
| 51 | .......... | .......... | .......... | .......... | .......... |
| 101 | .......... | .......... | .......... | .......... | .......... |
| 151 | .......... | .......... | .......... | .....AGC | TTCACCACAG |
| 201 | CAAGCACCAC | GCCGCCTACG | TCGCTGGCGC | CAACGCCGCC | CTGGAGGCCC |
| 251 | TCGCCGCCGC | CCGCGAGGAC | GGCGACCTGG | GTGCGATCAA | CCTGTGGGAG |
| 301 | AAGAACCTCG | CCTTCAACCT | GGGCGGCCAC | ACCAACCACT | CCGTGTTCTG |
| 351 | GAAGAACCTC | TCCCCCAACG | GCGGCGGCCA | GCCCGAGGGC | GAGCTCGCCG |
| 401 | AGGCCATCAA | GGACTCCTTC | GGCTCCTTCG | AGAAGTTCCA | GGCGCAGTTC |
| 451 | ACCGCCACCG | CCCTGGGCAT | CCAGGGCTCG | GGCTGGGCCG | TGCTCGCCTA |
| 501 | CGACTCAATC | TCCGGCAAGC | TGCTGATCTT | CCAGCTCTTC | GACCAGCAGG |
| 551 | CCAACGTGCC | CGTGGGCACG | ACCCCGCTGT | TCATGGTGGA | CATGTGGGAG |
| 601 | CACGCATTCT | ACCTCGACTA | CCTCAACGTC | AAGGCCGACT | ACGTCAAGGC |
| 651 | CATCTGGAAC | GTCGTGAACT | GGGACGAT.. | .......... | .......... |
| 701 | .......... | .......... | .......... | .......... | .......... |
| 751 | .......... | .......... | .......... | .......... | .......... |

TABLE 17

Mismatchanalysis for PCR Primer Z261 (X = number of mismatches)

| Z261 | 5'-CCA ARC TCG AAG AGG CGC GSG CCA A-3' | X |
|------|------------------------------------------|---|
| M. avium | 5'-... ... ... ... ... .C. ... ... .-3' | 1 |
| M. fortuitum | 5'-... ... ... .T. ... ... ... ... .-3' | 1 |
| M. gordonae | 5'-... ... .G. ... .A. ... ... ... .-3' | 2 |
| M. intrac. | 5'-... ... ... ... ... .C. .T. ... .-3' | 2 |
| M. kansasii | 5'-... ... ... ... ... ... ... ... .-3' | 0 |
| M. scroful. | 5'-... ... ..C ... ... A.. ... ... .-3' | 2 |
| M. simiae | 5'-... ... .T. ... ... ... ... ... .-3' | 1 |
| M. tuberculosis | 5'-... ... ... ... ... ... ... ... .-3' | 0 |
| M. xenopi | 5'-... ... .G. .G. ... ... ... ... .-3' | 2 |
| A. viscosus | 5'-AGG CC. ... CC. CC. .C. ... AGG .-3' | 13 |
| C. diphth. | 5'-AG. ... .GC ..A ... .T. ... AG. .-3' | 8 |
| C. ps. dipht. | 5'-A.G CT. .G. ... .A. A.. ...A A.G .-3' | 11 |
| Nocardia | 5'-AG. ... .G. ... CC. .C. .T. AGG C-3' | 11 |
| Human* | 5'-GG. ... ATT ..A G.A .TG A.T GA. G-3' | 15 |
| E. coli** | 5'-AA. GC. .GC C.. .AT TTG C.A A.C T-3' | 17 |

*taken from sequence AC M123267/**taken from sequence AC X03951 EMBL Data Bank, Heidelberg, FRG, and GenBank, Los Alamos, USA

TABLE 18

| Consensus sequence: | 5'-GAC AAG CCS ACS GGH GAN YTS GCC GCV GCS ATC GMY G-3' |
|---|---|
| A. viscosus | 5'-.G. C.. ... GA. .. .. .. .A. ... ... A.G .-3' |
| C. diphth. | 5'-.G. GGC GA. C.A AC. .G. GCT TTG ..T .A. GCA AT. .-3' |
| C. ps. dipht. | 5'-.G. G.. ..A ... ... ... ..A ..A .A. ..T ... ... C-3' |
| N. asteroides | 5'-... ... ... GT. ... ... ... ... ... ... ... .-3' |
| E. coli | 5'-AC. .CC .T. CA. ... ... ... AAA ... ..T ... ..A C-3' |
| Human | 5'-.TG ... GT. TG. ... AG. A.T AAA .G. CT. .CT ..A .-3' |

| Individual oligonucleotides constituting the pool of genus-specific probes: | |
|---|---|
| Z310 M. tuberc. | 5'-GAC AAG CCC ACC GGC GAA CTC GCC GCA GCC ATC GCC G-3' |
| Z311 M. intrac. M. xenopi | 5'-GAC AAG CCG ACC GGC GAA TTG GCC GCC GCS ATC GAC G-3' |
| Z312 M. avium | 5'-GAC AAG CCC ACC GGT GAG CTG GCC GCC GCG ATC GAC G-3' |
| Z313 M. gord. | 5'-GAC AAG CCG ACC GGT GAC CTG GCC GCC GCG ATC GAC G-3' |
| Z314 M. fort. | 5'-GAC AAG CCG ACG GGC GAT CTG GCC GCG GCG ATC GAC G-3' |
| Z315 M. scroful. | 5'-GAC AAG CCG ACC GGA GAA CTG GCC GCC GCG ATC GAT G-3' |

TABLE 18-continued

| | |
|---|---|
| Z316 M. simiae | 5'-GAC AAG CCG ACC GGA GAT CTC GCC GCC GCC ATC GAC G-3' |
| Z317 M. kans. | 5'-GAC AAG CCG ACC GGC GAA CTC GCC GCG GCC ATC GAC G-3' |

---

I claim:

1. A method for determining the presence or absence of organisms of the genus Mycobacterium, comprising:
 (a) amplifying a target region of a nucleic acid sequence of a superoxide dismutase (SOD) gene of said organisms using a pair of oligonucleotide primers consisting of the sequences 5'-CCAARCTCGAAGAGGCGCGS-GCCAA-3'(SEQ ID NO:3), 5'-TCGKCCCAGTTCAC-GACRTTCCA-3'(SEQ ID NO:2), or the complementary sequences thereto;
 (b) treating the amplified target region with an oligonucleotide probe containing a sequence that is sufficiently complementary to the sequence of the amplified target region to hybridize therewith; and
 (c) detecting hybrids formed, if any, between said amplified target region and said oligonucleotide probe, whereby the presence or absence of the Mycobacteria is determined.

2. The method of claim 1, wherein the target region is amplified by means of a polymerase chain reaction (PCR).

3. The method of claim 2, wherein said probe consists of the sequence 5'-GACAAGCCSACSGGHGANYTSGC-CGCVGCSATCGMYG-3'(SEQ ID NO:4), or a sequence complementary thereto.

4. The method of claim 3, wherein said probe is selected from the group consisting of 5'-GACAAGCCCACCGGC-GAACTCGCCGCAGCCATCGCCG-3'(SEQ ID NO:5), 5'-GACAAGCCGACCGGCGAATTGGCCGC-CGCSATCGACG-3'(SEQ ID NO:6), 5'-GACAAGC-CCACCGGTGAGCTGGCCGCCGCGATCGACG-3'(SEQ ID NO:7), 5'-GACAAGCCGACCGGTGACCTGGCCGC- CGCGATCGACG-3'(SEQ ID NO:8), 5'-GACAAGC-CGACGGGCGATCTGGCCGCGGCGATCGACG-3'(SEQ ID NO:9), 5'-GACAAGCCGACCGGAGAACTGGCCGC-CGCGATCGATG-3'(SEQ ID NO:10, 5'-GACAAGC-CGACCGGAGATCTCGCCGCCGCCATCGACG-3'(SEQ ID NO:11), 5'-GACAAGCCGACCGGCGAACTCGC-CGCGGCCATCGACG-3'(SEQ ID NO:12), and sequences complementary to each of the foregoing sequences.

5. The method of claim 2, wherein the oligonucleotide probe hybridizes to a region of the amplified target nucleic acid sequence of the SOD gene, which region varies between species of Mycobacterium, thereby facilitating the differentiation between said species of Mycobacterium.

6. The method of claim 5, wherein the oligonucleotide probe hybridizes to a region of the target nucleic acid sequence of the SOD gene of the species M. intracellulare and not to a species other than M. intracellulare.

7. The method of claim 6, wherein said probe consists of the sequence 5'-CCTTCGGATCCTTCGACCGGTTC-CGCGCGCAGTTCAG-3'(SEQ ID NO:13), or a sequence complementary thereto.

8. The method of claim 5, wherein the oligonucleotide probe hybridizes to a region of the target nucleic acid sequence of the SOD gene of the species M. avium and M. brunense and not to a species other than M. avium and M. brunense.

9. The method of claim 8, wherein said probe consists of the sequence 5'-GTCCTTCGACAAGTTCCGAGCG-CAATTCAGCGCCGCC-3'(SEQ ID NO:14), or a sequence complementary thereto.

10. The method of claim 5, wherein the oligonucleotide probe hybridizes to a region of the target nucleic acid sequence of the SOD gene of the species *M. gordonae* and not to a species other than *M. gordonae*.

11. The method of claim 10, wherein said probe consists of the sequence 5'-TCTGGGCGGCCGGTTGCTCAC-CTTT-3'(SEQ ID NO:15), or a sequence complementary thereto.

12. The method of claim 5, wherein the oligonucleotide probe hybridizes to a region of the target nucleic acid sequence of the SOD gene of the species *M. simiae* and not to a species other than *M. simiae*.

13. The method of claim 12, wherein said probe consists of the sequence 5'-GTCCCCGAACGGCGGAGACAAGC-CGACCGGAGATCTC-3'(SEQ ID NO:16), or a sequence complementary thereto.

14. The method of claim 5, wherein the oligonucleotide probe hybridizes to a region of the target nucleic acid sequence of the SOD gene of the species *M. tuberculosis* and not to a species other than *M. tuberculosis*.

15. The method of claim 14, wherein said probe consists of the sequence selected from the group consisting of 5'-GCTAGGCATTGTTCCGCTGCTGCTGC-3'(SEQ ID NO:17), 5'-AGTCGACTTTGCCAAGGCGTTT-3'(SEQ ID NO:23), 5'-ACGAACTTCCCGCTAGGCATTGTTC-CGCTGCTGCTGC-3'(SEQ ID NO:22), and a sequence complementary to each of the foregoing sequences.

16. The method of claim 5, wherein the oligonucleotide probe hybridizes to a region of the target nucleic acid sequence of the SOD gene of the species *M. xenopi* and not to a species other than M. xenopi.

17. The method of claim 16, wherein said probe consists of the sequence 5'-TCCGCGATCGTCGGGCATGAGAAG-GCCCTCGCGTTCA-3'(SEQ ID NO:18), or a sequence complementary thereto.

18. The method of claim 5, wherein the oligonucleotide probe hybridizes to a region of the target nucleic acid sequence of the SOD gene of the species *M. kansasii* and not to a species other than *M. kansasii*.

19. The method of claim 18, wherein said probe consists of the sequence 5'-CCAGACGAACTTTCCACTCGGA-3'(SEQ ID NO:19), or a sequence complementary thereto.

20. The method of claim 5, wherein the oligonucleotide probe hybridizes to a region of the target nucleic acid sequence of the SOD gene of the species *M. scrofulaceum* and not to a species other than *M. scrofulaceum*.

21. The method of claim 20, wherein said probe consists of the sequence 5'-TGACACACTCGGCAGCAGGCT-GCTCACCTTCCAGCTT-3'(SEQ ID NO:20), or a sequence complementary thereto.

22. The method of claim 5, wherein the oligonucleotide probe hybridizes to a region of the target nucleic acid sequence of the SOD gene of the species *M. fortuitum* and not to a species other than *M. fortuitum*.

23. The method of claim 22, wherein said probe consists of the sequence 5'-ACGACAGCCTGGGCGATCGGCT-3'(SEQ ID NO:21 ), or a sequence complementary thereto.

24. An oligonucleotide primer consisting of the sequence 5'-AGCTTCACCACAGCAAGCACCA-3'(SEQ ID NO:1), or a sequence complementary thereto.

25. An oligonucleotide primer consisting of the sequence 5'-TCGKCCCAGTTCACGACRTTCCA-3'(SEQ ID NO:2), or a sequence complementary thereto.

26. An oligonucleotide primer consisting of the sequence 5'-CCAARCTCGAAGAGGCGCGSGCCAA-3'(SEQ ID NO:3), or a sequence complementary thereto.

27. A set of reagents for amplifying a part of a gene coding for SOD of a Mycobacterium species, comprising a first primer consisting of the sequence 5'-CCAARCTCGAA-GAGGCGCGSGCCAA-3'(SEQ ID NO:3), or a sequence complementary thereto, and a second primer consisting of the sequence 5'-TCGKCCCAGTTCACGACRTTCCA-3'(SEQ ID NO:2), or a sequence complementary thereto.

28. A set of reagents for detecting a Mycobacterial species consisting of an oligonucleotide probe containing the sequence 5'GACAAGCCSACSGGHGANYTSGC-CGCVGCSATCGMYG-3'(SEQ ID NO:4), or a sequence complementary thereto.

29. The set of reagents of claim 28, wherein the probe is selected from the group consisting of 5'-GACAAGCCCAC-CGGCGAACTCGCCGCAGCCATCGCCG-3'(SEQ ID NO:5), 5'-GACAAGCCGACCGGCGAATTGGCCGC-CGCSATCGACG-3'(SEQ ID NO:6), 5'-GACAAGC-CCACCGGTGAGCTGGCCGCCGCCGATCGACG-3'(SEQ ID NO:7), 5'-GACAAGCCGACCGGTGACCTGGCCGC-CGCGATCGACG-3'(SEQ ID NO:8), 5'-GACAAGC-CGACGGGCGATCTGGCCGCGGCGATCGACG-3'(SEQ ID NO:9), 5'-GACAAGCCGACCGGAGAACTGGCCGC-CGCGATCGATG-3'(SEQ ID NO:10), 5'-GACAAGC-CGACCGGAGATCTCGCCGCCGCCATCGACG-3'(SEQ ID NO:11), 5'-GACAAGCCGACCGGCGAACTCGC-CGCGGCCATCGACG-3'(SEQ ID NO:12), and sequences complementary to each of the foregoing sequences.

30. A set of reagents for differentiating among various species of Mycobacteria, comprising for each said species a probe capable of hybridizing to a part of a gene coding for superoxide dismutase for each said Mycobacterial species, wherein the probe consists of a sequence selected from 5'-CCTTCGGATCCTTCGACCGGTTC-CGCGCGCAGTTCAG-3'(SEQ ID NO:13), 5'-GTCCTTC-GACAAGTTCCGAGCGCAATTCAGCGCCGCC-3'(SEQ ID NO:14), 5'-TCTGGGCGGCCGGTTGCTCACCTTT-3'(SEQ ID NO:15), 5'-GTCCCCGAACGGCGGAGA-CAAGCCGACCGGAGATCTC-3'(SEQ ID NO:16), 5'-GCTAGGCATTGTTCCGCTGCTGCTGC-3'(SEQ ID NO:17), 5'-TCCGCGATCGTCGGGCATGAGAAGGC-CCTCGCGTTCA-3'(SEQ ID NO:18), 5'-CCAGAC-GAACTTTCCACTCGGA-3'(SEQ ID NO:19), 5'-TGACA-CACTCGGCAGCAGGCTGCTCACCTTCCAGCTT-3'(SEQ ID NO:20), 5'-ACGACAGCCTGGGCGATCGGCT-3'(SEQ ID NO:21), 5'-ACGAACTTCCCGCTAGGCATTGTTC-CGCTGCTGCTGC-3'(SEQ ID NO:22), 5'-AGTC-GACTTTGCCAAGGCGTTT-3'(SEQ ID NO:23), or the complementary sequences to each of the foregoing sequences.

31. A set of reagents for amplifying and detecting a part of a gene coding for SOD of a Mycobacterium species, comprising:

a first primer consisting of the sequence 5'-CCAARCTC-GAAGAGGCGCGSGCCAA-3'(SEQ ID NO:3), or a sequence complementary thereto;

a second primer consisting of the sequence 5'-TCGKC-CCAGTTCACGACRTTCCA-3'(SEQ ID NO:2), or a sequence complementary thereto; and a probe capable of hybridizing to a part of a gene coding for SOD of a Mycobacterial species and differentiating between Mycobacterial species.

32. The set of reagents of claim 31, wherein said probe is selected from the group consisting of 5'-CCTTCGGATC-CTTCGACCGGTTCCGCGCGCAGTTCAG-3'(SEQ ID NO:13), 5'-GTCCTTCGACAAGTTCCGAGCGCAAT-TCAGCGCCGCC-3'(SEQ ID NO:14), 5'-TCTGGGCGGC-CGGTTGCTCACCTTT-3'(SEQ ID NO:15), 5'-GTC-CCCGAACGGCGGAGACAAGCCGACCGGAGATCTC-3'(SEQ ID NO:16), 5'-GCTAGGCATTGTTCCGCTGCTGCTGC-3'(SEQ ID NO:17), 5'-TCCGCGATCGTCGGGCATGAGAAGGC-CCTCGCGTTCA-3'(SEQ ID NO:18), 5'-CCAGAC-GAACTTTCCACTCGGA-3'(SEQ ID NO:19), 5'-TGACA-CACTCGGCAGCAGGCTGCTCACCTTCCAGCTT-3'(SEQ ID NO:20), 5'-ACGACAGCCTGGGCGATCGGCT-3'(SEQ ID NO:21), 5'-ACGAACTTCCCGCTAGGCATTGTTC-CGCTGCTGCTGC-3'(SEQ ID NO:22), 5'-AGTC-GACTTTGCCAAGGCGTTT-3'(SEQ ID NO:23), and sequences complementary to each of the foregoing sequences.

33. A set of reagents for amplifying and detecting a part of a gene coding for superoxide dismutase (SOD) of pathogenic and nonpathogenic organisms of the genus Mycobacterium, comprising:

a first primer consisting of the sequence 5'-CCAARCTC-GAAGAGGCGCGSGCCAA-3'(SEQ ID NO:3), or a sequence complementary thereto;

a second primer consisting of the sequence 5'-TCGKC-CCAGTTCACGACRTTCCA-3'(SEQ ID NO:2), or a sequence complementary thereto; and a probe capable of hybridizing to a part of an amplified section of a gene coding for SOD of a bacterial species in the genus Mycobacterium.

34. The set of reagents of claim 33, wherein said probe is selected from the group consisting of 5'-GACAAGCCCAC-CGGCGAACTCGCCGCAGCCATCGCCG-3'(SEQ ID NO:5), 5'-GACAAGCCGACCGGCGAATTGGCCGC-CGCSATCGACG-3'(SEQ ID NO:6), 5'-GACAAGC-CCACCGGTGAGCTGGCCGCCGCGATCGACG-3'(SEQ ID NO:7), 5'-GACAAGCCGACCGGTGACCTGGCCGC-CGCGATCGACG-3'(SEQ ID NO:8), 5'-GACAAGC-CGACGGGCGATCTGGCCGCGGCGATCGACG-3'(SEQ ID NO:9), 5'-GACAAGCCGACCGGAGAACTGGCCGC-CGCGATCGATG-3'(SEQ ID NO:10, 5'-GACAAGC-CGACCGGAGATCTCGCCGCCGCCATCGACG-3'(SEQ ID NO:11), 5'-GACAAGCCGACCGGCGAACTCGC-CGCGGCCATCGACG-3'(SEQ ID NO:12), and sequences complementary to each of the foregoing sequences.

35. An oligonucleotide probe consisting of a sequence selected from the group consisting of 5'-GACAAGCCSAC-SGGHGANYTSGCCGCVGCSATCGMYG-3'(SEQ ID NO:4), 5'-GACAAGCCCACCGGCGAACTCGCCG-CAGCCATCGCCG-3'(SEQ ID NO:5), 5'-GACAAGC-CGACCGGCGAATTGGCCGCCGCSATCGACG-3'(SEQ ID NO:6), 5'-GACAAGCCCACCGGTGAGCTGGCCGC-CGCGATCGACG-3'(SEQ ID NO:7), 5'-GACAAGC-CGACCGGTGACCTGGCCGCCGCGATCGACG-3'(SEQ ID NO:8), 5'-GACAAGCCGACGGGCGATCTGGC-CGCGGCGATCGACG-3'(SEQ ID NO:9), 5'-GACAAGC-CGACCGGAGAACTGGCCGCCGCGATCGATG-3'(SEQ ID NO:10, 5'-GACAAGCCGACCGGAGATCTCGCCGC-CGCCATCGACG-3'(SEQ ID NO:11), 5'-GACAAGC-CGACCGGCGAACTCGCCGCGGCCATCGACG-3'(SEQ ID NO:12), 5'-CCTTCGGATCCTTCGACCGGTTC-CGCGCGCAGTTCAG-3'(SEQ ID NO:13), 5'-GTCCTTC-GACAAGTTCCGAGCGCAATTCAGCGCCGCC-3'(SEQ ID NO:14), 5'-TCTGGGCGGCCGGTTGCTCACCTTT-3'(SEQ ID NO:15), 5'-GTCCCCGAACGGCGGAGA-CAAGCCGACCGGAGATCTC-3'(SEQ ID NO:16), 5'-GCTAGGCATTGTTCCGCTGCTGCTGC-3'(SEQ ID NO:17), 5'-TCCGCGATCGTCGGGCATGAGAAGGC-CCTCGCGTTCA-3'(SEQ ID NO:18), 5'-CCAGAC-GAACTTTCCACTCGGA-3'(SEQ ID NO:19), 5'-TGACA-CACTCGGCAGCAGGCTGCTCACCTTCCAGCTT-3'(SEQ ID NO:20), 5'-ACGACAGCCTGGGCGATCGGCT-3'(SEQ ID NO:21), 5'-ACGAACTTCCCGCTAGGCATTGTTC-CGCTGCTGCTGC-3'(SEQ ID NO:22), 5'-AGTC-GACTTTGCCAAGGCGTTT-3'(SEQ ID NO:23), and the complementary sequences thereto.

* * * * *

UNITED STATES PATENT AND TRADEMARK OFFICE
CERTIFICATE OF CORRECTION

PATENT NO. : 5,525,463
DATED : June 11, 1996
INVENTOR(S) : Werner Zolg It is certified that error appears in the above-identified patent and that said Letters Patent is hereby corrected as shown below:

In claim 2, column 59, line 56, delete the "a" before the word "polymerase".

Signed and Sealed this

Ninth Day of September, 1997

Attest:

BRUCE LEHMAN

*Attesting Officer*    *Commissioner of Patents and Trademarks*